United States Patent [19]

Kmiec et al.

[11] Patent Number: 5,760,012
[45] Date of Patent: Jun. 2, 1998

[54] METHODS AND COMPOUNDS FOR CURING DISEASES CAUSED BY MUTATIONS

[75] Inventors: Eric B. Kmiec, Malvern; Allyson Cole-Strauss, Philadelphia; Kyonggeun Yoon, Berwyn, all of Pa.

[73] Assignee: Thomas Jefferson University, Philadelphia, Pa.

[21] Appl. No.: 640,517

[22] Filed: May 1, 1996

[51] Int. Cl.$^6$ .............................. A61K 48/00; C12Q 1/68; C12N 15/11
[52] U.S. Cl. .............................. 514/44; 435/6; 435/172.3; 435/320.1; 435/325; 435/366; 435/372; 536/23.1; 536/25.1
[58] Field of Search ........................ 800/2, DIG. 2, 800/DIG. 3; 435/6, 172.3, 320.1, 316, 325, 372; 536/23.1, 25.1; 935/2, 3, 6, 22, 24, 76; 514/44

[56] References Cited

PUBLICATIONS

A. Cole–Strauss et al, Science 273: 1386–9 ('96).

*Primary Examiner*—John L. LeGuyader
*Attorney, Agent, or Firm*—Daniel Hansburg; Thomas E. Friebel

[57] ABSTRACT

The invention concerns the use of duplex oligonucleotides having both 2'-deoxyribonucleotides and ribonucleotides, wherein there is base pairing between the two types of nucleotides. The sequence of the oligonucleotide is selected so that the 3' and 5' most regions of the oligonucleotide are homologous with (identical to) the sequence of a preselected target gene of a cell. The two regions of homology embrace a region that is heterologous with the target sequence. The introduction of the oligonucleotide into the nucleus of the cell causes the alteration of the target gene such that the sequence of the altered target gene is the sequence of the heterologous region. Consequently, the oligonucleotides of the invention are termed Chimeric Repair Vectors (CRV). In one embodiment of the invention the target gene is a globin gene and the target cell is a hematopoietic stem cell. This embodiment can be used to correct certain hemoglobinopathies such as Sickle Cell Disease, β-thalassemia, and also Gaucher Disease. The rate of correction of the globin gene is high enough so that no selection of the treated hematopoietic stem cells is required to obtain a therapeutically significant effect. In one embodiment the ribose moieties of the nucleotides of the CRV contain methylated 2'-oxygens.

25 Claims, 7 Drawing Sheets

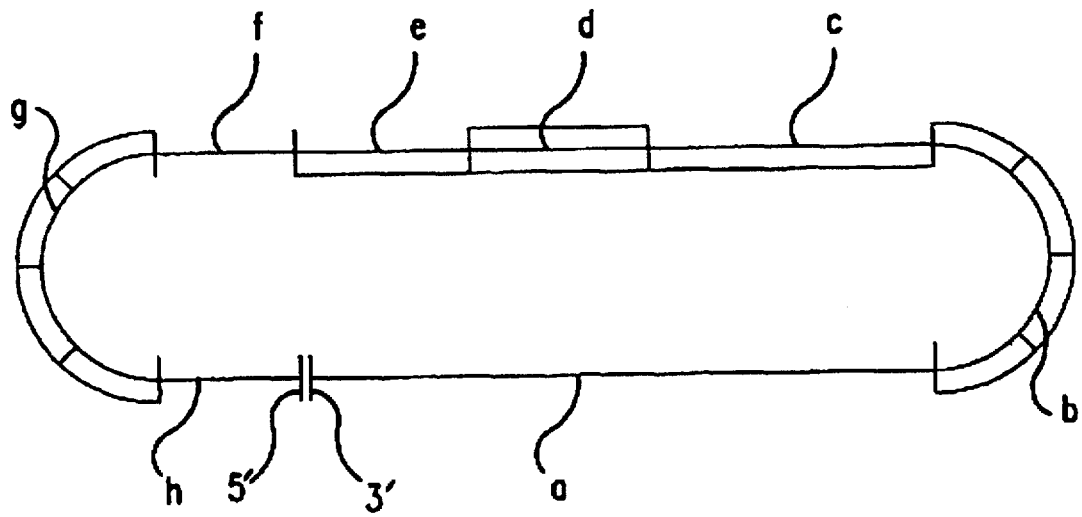
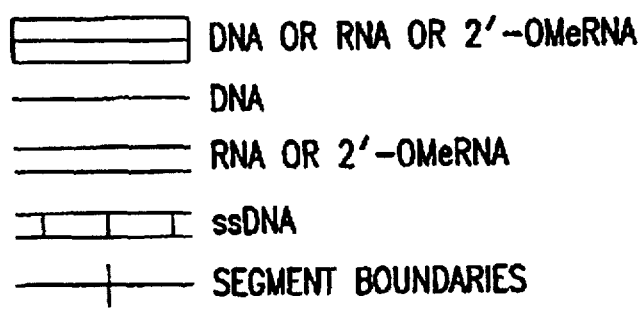
FIG.1

```
      TGCGCG-ucgcggcggaTGCGGgugagccgacT
    T                                  T
    T     3'5'                         T           Ch1
      TCGCGC AGCGCCGCCTACGCCCACTCGGCTGT TGCGCG-ucgcggcggaTGTGGgugagccgacT
    T                                  T
    T     3'5'                         T           Ch2
      TCGCGC AGCGCCGCCTACACCCACTCGGCTGT TCGCGC-agcgccgccuACGCCcacucggcugT
    T                                  T
    T     5'3'                         T           Ch3
      TGCGCG TCGCGGCGGATGCGGGTGAGCCGACT TGCGCG-TCGCGGCGGATGCGGGTGAGCCGACT
    T                                  T
    T     3'5'                         T           Dh1
    T TCGCGC AGCGCCGCCTACGCCCACTCGGCTGT T
```

FIG.2A

```
                    *
    →    T
        AC CTG ACT CCT GTG GAG AAG TCT GC           βS

TG GAC TGA GGA CAC CTC TTC AGA CG
                    *
        AC CTG ACT CCT GAG GAG AAG TCT GC           βA

TG GAC TGA GGA CTC CTC TTC AGA CG
                    *
        AT CTG ACT CCT GAG GAG AAG ACT GC           δ
         ‾                              ‾
        TA GAC TGA GGA CTC CTC TTC TGA CG
        ‾                          ‾
                    *
  T T GCGCG ug gac uga ggA CTC Cuc uuc aga cg T T      SC1
  T T CGCGC AC CTG ACT CCT GAG GAG AAG TCT GC T T    βS→βA
          3′5′
                    *
  T T GCGCG ug gac uga ggA CAC Cuc uuc aga cg T T      SC2
  T T CGCGC AC CTG ACT CCT GTG GAG AAG TCT GC T T    βA→βS
          3′5′
                    *
  T T GCGCG ua gac uga ggA CTC Cuc uuc uga cg T T      SC3
        ‾                           ‾
  T T CGCGC AT CTG ACT CCT GAG GAG AAG ACT GC T T   3 MISMATCHES TO
          ‾                              ‾              βS
          3′5′           *
  T T GCGCG ug gac uga ggA CTC Cuc uuc uga cg T T      SC4
                                        ‾
  T T CGCGC AC CTG ACT CCT GAG GAG AAG ACT GC T T   2 MISMATCHES TO
                                          ‾             βS
          3′5′
  T T CGCGC ac cug acu ccT GTG Gag aag ucu gc T T      SC5
  T T GCGCG TG GAC TGA GGA CAC CTC TTC AGA CG T T   TARGETS THE NON-
          5′3′                                     TEMPLATE STRAND OF
                                                         βA
```

FIG.3

METHODS AND COMPOUNDS FOR CURING DISEASES CAUSED BY MUTATIONS

FIELD OF THE INVENTION

The field of the invention concerns cures for diseases caused by mutations that result abnormal levels of or products of the mutated gene in hematopoietic cells or any other cell-type that can be removed from a subject, cultured and reimplanted. The cure is effected by pairing the mutated gene of the subject by homologous recombination between the mutated gene and a chimeric repair vector (CRV), which is an nucleic acid having both deoxyribonucleotides and ribonucleotides. More particularly, the field concerns the repair of the mutations that cause Sickle Cell Disease, β-thalassemia and Gaucher Disease.

BACKGROUND OF THE INVENTION

A. Diseases Caused by Mutations of Genes Expressed by Hematopoietic Cells and Their Treatment by Bone Marrow Transplantation 1. Hemoglobinopathies and Gaucher Disease There are over 500 known structural variants of hemoglobin. Most persons having a variant hemoglobin are asymptomatic or only mildly affected. Three common variants are associated with significant disease. Two, HbS (Sickle Hemoglobin) and HbC, are point mutations in the codon encoding $Glu^6$ of β-globin and are found in Africans and their descendants. HbC results from the substitution G→A in the first position of codon 6 and HbS results from the substitution A→T in the second position of codon 6, producing $Lys^6$ and $Val^6$ respectively. The third common structural variant of hemoglobin associated with disease, HbE, results from the substitution G→A in the first position of codon 26, encoding $Glu^{26}$ resulting in a $Lys^{26}$ and is found primarily in the Southeast Asian population and their descendants.

Persons heterozygous for HbS, HbC or HbE do not have significant symptoms. However, HbS homozygotes, HbS/HbC heterozygotes, and heterozygotes for HbC or HbE and an allele of β-thalassemia are severely effected and require frequent medical attention.

Thalassemias are a class of hemoglobinopathies wherein there is an imbalance between the rate of synthesis α-globin and β-globin. The thalassemias are classified according to the mutated gene, α or β, and whether there is a complete, e.g., $\alpha^\circ$ and $\beta^\circ$, or partial reduction, e.g., $\alpha^+$ and $\beta^+$, of the affected globin.

There are two functional α-globin genes in the haploid human genome, which are closely linked. The most common causes of α-thalassemia are deletions or rearrangements of the linked α-globin genes or of the α-globin locus control region.

By contrast the common causes of β-thalassemia are point mutations. The most common cause is a G→A substitution at position of 110 of the β-globin gene, which creates a novel splice acceptor site in the first intron (IVS1).

About 100 different types β-thalassemia have been characterized. Of the characterized mutations only 14 are dominant, i.e., cause a significant clinical condition when heterozygous with a wild-type β-globin allele. The remaining mutations lead to a severe clinical condition, termed thalassemia major, when homozygous or when heterozygous with a second β-thalassemia gene. A detailed review of Hemoglobinopathies is found at Weatherall et al. in THE METABOLIC AND MOLECULAR BASIS OF INHERITED DISEASE 7th Ed., Chapter 113 (McGraw-Hill, New York, 1995)

Gaucher Disease is a lysosomal glycolipid storage disease. There are three recognized types. Type 1 Gaucher Disease is most prevalent in Ashkenazic (Eastern European) Jews and their descendants; Type 2 is panethnic and Type 3 is most prevalent in Northern Sweden. The cause of Gaucher Disease is a defect in the enzyme glucocerebrosidase, also termed acid β-glucosidase. Glucocerebrosidase is expressed in the macrophage/monocyte cell-type, which originate from the bone marrow.

There are three different, common mutations that cause Gaucher Disease: an A→G substitution at nucleotide 1226 of the mRNA, which causes a Asn→Ser substitution at residue 370 of glucocerebrosidase (the N370S mutation); a T→C substitution at nucleotide 1448 of the mRNA, which causes a Leu→Pro substitution at residue 444 of glucocerebrosidase (the L444P mutation); and a duplication of a $G^{84}$ nucleotide which results in a frameshift mutation (the 84GG mutation). The N370S and 84GG mutations are associated with the Ashkenazic population while the L444P mutation is associated with the Northern Swedish population and with sporadic mutations.

Uncommon, but not rare, mutations in the coding sequence that cause Gaucher Disease have been identified as follows: at 754, T→A; at 1192, C→T; at 1193, G→A; at 1297, G→T; at 1342, G→C; at 1504, C→T; and at 1604, G→A.

The mutations that cause Gaucher Disease are recessive, i.e., an individual with one wild-type glucocerebrosidase allele is asymptomatic. Individuals which are homozygous for the N370S mutation frequently develop only a mild form of the disease late in life. By contrast, individuals homozygous for the L444P mutation have the more severe Type 2 and Type 3 Gaucher Disease. The 84GG mutation results in a product with no enzymatic activity and results in severe clinical disease in the homozygous state. Of the uncommon mutations, the mutations at nucleotides 754, 1192, 1297 and 1342 are associated with severe forms of the disease. A detailed review of Gaucher Disease can be found in Beutler, E. & Grabowski in THE METABOLIC and MOLECULAR BASIS OF INHERITED DISEASE 7th Ed., Chapter 86 (McGraw-Hill, New York, 1995).

2. The Treatment of Diseases Caused by Mutations by Bone Marrow Transplantation

The treatment of severe cases of β-thalassemia and sickle anemia by allogenic bone marrow transplantation from HLA-matched bone marrow having a normal β-globin gene has been reported to have clinical benefits. Giardini, C., et al., 1995, Annu. Rev. Med. 46:319–30(thalassemia); Lucarelli, G., et al., 1991 Hematol. Oncol. Clin. North Am. 5:549 (thalassemia); Kalinyak, K. A., et al., 1995, Am. J. of Hemat. 48:256–61 (sickle cell); Abboud, M. R., et al., 1994, Am. J. of Ped. Hem/Onc 16:86–89 (sickle cell); Kirkpatrick, D. V., et al., 1991, Semin. Hematol. 28:240 (sickle cell). The clinical results indicate that engraftment, when successful, is curative. Engraftment can be persistent; reports of 3 to 8 year follow-up periods without rejection are found. However, there is a significant failure rate due to the development of graft versus host disease and maintenance doses of immunosuppressive drugs such as cyclosporin are needed. There can also be significant difficulties in obtaining HLA-matched bone marrow.

Allogeneic bone marrow transplantation for the treatment of Type 1 Gaucher Disease has yielded substantially equivalent results to those described above for thalassemia. Ringden, O., et. al., 1995, Transplantation 59:864; Chan, K. W., et al., 1994, Bone Marrow Transplantation 14:327. The use of bone marrow transplantation to treat the more severe Types 2 and 3 Gaucher Disease, which have central nervous system involvement, also has been reported to have favorable outcomes. Tsai, P., et al., 1992, Pediatr. Res. 31:503; Svennerholm, L., et al., 1991, Dev. Neurosci. 13:345–51. In contrast to the globin genes, an effective level of expression of glucocerebrosidase can be obtained by use of viral expression vectors, which suggests that autotransplantation of transduced bone marrow can be an effective therapy for Gaucher Disease. Karlsson, S. & Correll, P. H., 1993, Bone Marrow Transplantation 11(Suppl 1):124–7.

B. Chimeric Oligonucleotides Having DNA●RNA Base Pairs

An oligonucleotide having complementary deoxyribonucleotides and ribonucleotides and containing a sequence homologous to a fragment of the bacteriophage M13mp19, was described in Kmiec, E., et al., November 1994, Mol. and Cell. Biol. 14:7163–7172. The oligonucleotide had a single contiguous segment of ribonucleotides. Kmiec et al. showed that the oligonucleotide was a substrate for the REC2 homologous pairing enzyme from *Ustilago maydis*.

Patent publication Wo 95/15972, published Jun. 15, 1995, and corresponding U.S. patent application Ser. No. 08/353, 657, filed Dec. 9, 1994, described chimeric repair vectors (CRV) for the introduction of genetic changes in eukaryotic cells. Examples in a *Ustilago maydis* gene and in the murine ras gene were reported. The latter example was designed to introduce a transforming mutation into the ras gene so that the successful mutation of the ras gene in NIH 3T3 cells would cause the growth of a colony of cells ("transformation"). The WO 95/15972 publication reported that the maximum rate of transformation of NIH 3T3 was less than 0.1%, i.e., about 100 transformants per $10^6$ cells exposed to the ras CRV. In the *Ustilago maydis* system the rate of transformants was about 600 per $10^6$. A chimeric vector designed to introduce a mutation into a human bcl-2 gene was described in Kmiec, E. B., February 1996, Seminars in Oncology 23:188.

A CRV designed to repair the mutation in codon 12 of K-ras was described in Kmiec, E. B., December 1995, Advanced Drug Delivery Reviews 17:333–40. The CRV was tested in Capan 2, a cell line derived from a human pancreatic adenocarcinoma, using lipofectin to introduce the CRV into the Capan 2 cells. Twenty four hours after exposure to the CRV, the cells were harvested and genomic DNA was extracted; a fragment containing codon 12 of K-ras was amplified by PCR and the rate of conversion estimated by hybridization with allele specific probes. The rate of repair was reported to be approximately 18%.

A CRV designed to repair a mutation in the gene encoding liver/bone/kidney type alkaline phosphatase was reported in Yoon, K., et al., March 1996, Proc. Natl. Acad. Sci. 93:2071. The alkaline phosphatase gene was transiently introduced into CHO cells by a plasmid. Six hours later the CRV was introduced. The plasmid was recovered at 24 hours after introduction of the CRV and analyzed. The results showed that approximately 30 to 38% of the alkaline phosphatase genes were repaired by the CRV.

SUMMARY OF THE INVENTION

The present invention provides a method of curing a human subject's genetic disease that is caused by a mutation in a target gene. The invention encompasses the repair of a disease-causing mutation in a gene of a cell-type of a subject, wherein the cell-type can be removed from the subject, cultured and repaired ex vivo by introducing CRV into cells of the cell-type, and reimplanted in the subject, wherein the repair of the mutation in the reimplanted cell or its progeny is therapeutically effective. Generally the repair of greater than 25% of recessive mutations and the repair of greater than 50% of dominant mutations in a population of cells of a cell-type are therapeutically effective rates of repair.

In one embodiment of the invention the target gene is of the type that normally expressed in bone marrow cells or the progeny of bone marrow cells, collectively, hereinafter "hematopoietic cells." Thus, one embodiment of the invention is a method comprising the steps of placing hematopoietic stem cells (HSC) from the subject in a culture medium, introducing a chimeric repair vector (CRV) into the HSC to repair the target mutation and transplanting the CRV-containing HSC into the subject.

The invention encompasses the repair of any mutation other than large deletions or insertions, i.e., deletions or insertions of greater than about 6 bases, translocations and intrachromosomal rearrangements. In preferred embodiments the invention encompasses the repair of single base substitutions ("point mutations") and deletions or insertions of 1, 2 or 3 contiguous bases.

Further embodiments of the invention are the CRV, which are oligonucleotides of between about 40 and about 100 nucleotides, of which between about 12 and about 46 nucleotides have a 2' hydroxyl or 2'-hydroxylmethyl groups. The CRV comprises a segment having a sequence which is the same as the wild type sequence of the target gene that spans the mutation that causes the subject's disease. The CRV consist of an oligonucleotide, which is duplex, i.e., the nucleotide bases are Watson-Crick paired, except for two regions of about 4 unpaired nucleotides that allow the oligonucleotide to form hairpin ends. In particular embodiments, the invention encompasses CRV having the sequence of human glucocerebrosidase gene and globin genes and the human β-globin promoter.

BRIEF DESCRIPTION OF THE FIGURES

FIG. 1. General form of an embodiment of a Chimeric Repair Vector.

FIGS. 2A and 2B. FIG. 2A shows the sequence and structure of oligonucleotide Dh1 , (SEQ ID NO:91) and chimeric oligonucleotides Ch1, (SEQ ID NO:88) Ch2 (SEQ ID NO:89) and Ch3 (SEQ ID NO:90). FIG. 2B illustrates the relationship between the sequence of CRV Ch1 and the alkaline phosphatase gene (SEQ ID NO:92). DNA nucleotides are UPPER CASE; RNA nucleotides are lower case.

FIG. 3. The sequences of the codons 3–9 and adjacent dinucleotides of codons 2 and 10 of $\beta^S$-globin (nt 1–25 of SEQ ID NO:94), $\beta^A$-globin(nt 1–25 of SEQ ID NO:93), δ-globin (SEQ ID NO:98), and chimeric vectors SC1-SC5 (SEQ ID NO:93-97 respectively). DNA and RNA nucleotides are indicated as in FIG. 2A.

FIG. 4A and 4B show the fraction of copies of β-globin converted from $\beta^S$ to $\beta^A$ as a function of nM SC1 added and of $\beta^A$ to $\beta^S$ as a function nM of SC2, respectively, in cultures of EB-transformed lymphoblasts.

FIG. 5 shows the fraction of copies of β-globin converted $\beta^A$ to $\beta^S$ as a function of ng SC2 added to cultures of cd34⁺ hematopoietic stem cells.

DETAILED DESCRIPTION OF THE INVENTION

Figure 2B:
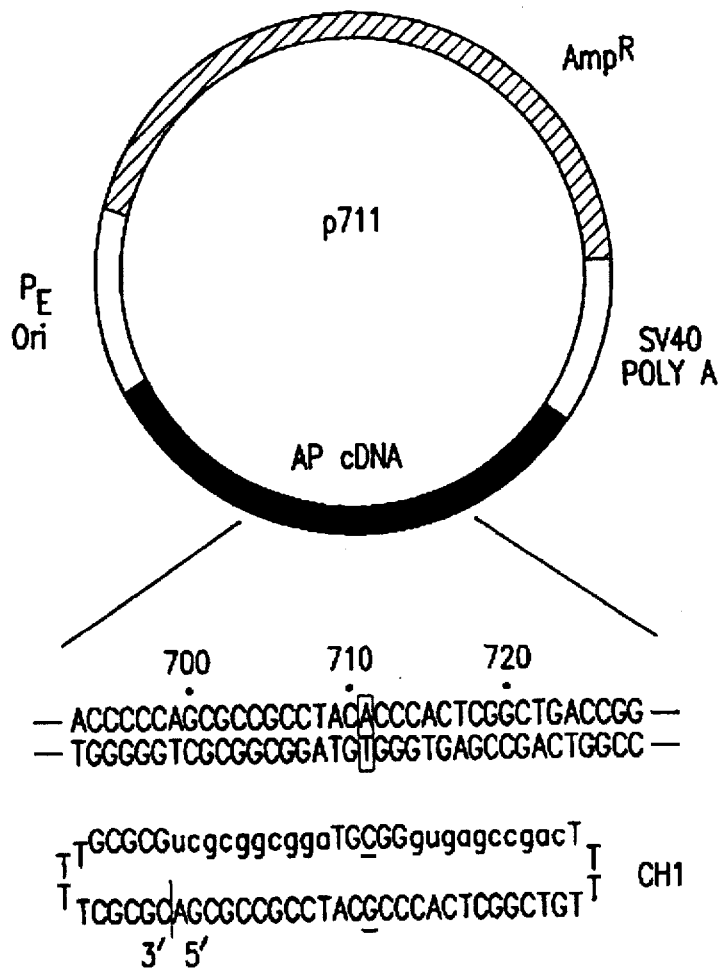

The invention provides Chimeric Repair Vectors (CRV) and a method of their use, termed "chimeroplasty," to correct a deleterious mutation in a non-transformed cell from a human subject of the type that can be transiently placed in a cell culture. Chimeroplasty is the process of placing a population of suitable cells (target cells) in culture, with or without undergoing growth, exposing the cultured cells to the CRV and reimplanted cells into the subject. The present invention is based, in part, on the discovery that the use of CRV according to the invention results in the repair of over 30% of the copies of the targeted gene and can result in the repair of over 50% of the copies of the targeted gene.

In one embodiment the target cells are hematopoietic cells and, particularly hematopoietic stem cells. As used herein hematopoietic cells includes both precursors and mature cells of the erythroid, lymphoid monocytoid (macrophage) and granulocytic lineages. As used herein hematopoietic stem cells (HSC) includes all cells found in either the bone marrow or the peripheral blood that can repopulate the bone marrow space and produce progeny of the hematopoietic lineage.

A. Diseases Susceptible to Treatment By the Invention

The present invention can be used to cure any genetic disease that is caused by the production of an abnormal gene product or over or under expression of a normal product in hematopoietic cells, which is caused by a mutation other than an large insertion or a deletion mutation or a intrachromosomal rearrangement or translocation.

An large insertion or deletion mutation is a mutation, in which more than six contiguous nucleotides are inserted or deleted compared to the normal or wild type sequence. Types of mutations that can be cured by the present invention include: any mutation caused by the replacement of a nucleotide by a different nucleotide, including replacements of up to 3 and up to 6 contiguous nucleotides; any mutation caused by the insertion or deletion of up to 3 contiguous nucleotides; and, alternatively, any mutation caused by the insertion or deletion of up to 6 contiguous nucleotides. The types of mutations that can be cured by the present invention are termed herein "CRV-repairable mutations."

A CRV-repairable mutation can be in any human gene. As used herein a gene refers to either a structural gene, e.g., exons and intervening sequences of a gene encoding a protein, or in a control element, e.g., a promoter or enhancer of a structural gene. The invention also encompasses the cure of diseases caused by several CRV-repairable mutations in the same gene. A single CRV can correct non-contiguous point mutations that are within about 30 nucleotides of each other. Alternatively, diseases can be treated by introducing mixtures of multiple CRV into the HSC of the subject such that each of the CRV-repairable mutations can be repaired by one CRV of the mixture. The invention encompasses CRV having a sequence which can repair any mutated human gene the expression or lack of expression or over expression of which in hematopoietic cells or progeny of HSC is a cause of a disease in subject. In one embodiment, the invention excludes the ras gene, see Taparowski, E., 1982, Nature 300:762; Sukumar, S., et al., 1983, Nature 306:658.; in an alternative embodiment the invention excludes the ras gene and the alkaline phosphatase gene, Weiss, M. J., et al., 1988, Proc. Natl. Acad. Sci. 85:7666.

Non-limiting examples of diseases that can be cured by the invention include: hemoglobinopathies caused by CRV-repairable mutations in a globin structural gene, such as sickle cell disease; β-thalassemia, a disease of under expression of the β-globin gene caused by a CRV-repairable mutation in the β-globin promoter or the β-globin structural gene; and the forms of Gaucher Disease that are caused by one or more CRV-repairable mutations in the glucocerebrosidase structural gene. As used herein the term "structural gene" refers to the DNA that encodes the gene product; the term "gene" includes regulatory sequences, i.e. promoters and enhancers, introns and exons. The term "sequence of a gene" refers to the sequence of the coding strand of a gene. The complement thereof is the sequence of the non-coding strand.

The location of the CRV-repairable mutation or mutations in any subject can be identified by techniques well known to those skilled in the art. The location of the mutation in Sickle Cell Disease (SCD) is in the codon encoding the 6th codon of the β-globin.

Except in the few conditions, where the location of the responsible point mutation is well known, the target gene from the subject to be treated should be sequenced to identify the location of the point mutation. For example more than 500 point mutations in globin genes have been described. (Bunn, H. F. & Forget, B. G., 1986, HEMOGLOBIN: MOLECULAR, GENETIC AND CLINICAL ASPECTS, W. B. Saunders, Phil.) Similarly no one mutation causes Gaucher Disease (Hong, C. M., et al., 1990, DNA Cell Biol. 9:233–41) or β-thalassemia (Kazazian, H. H., 1990, Seminars in Hematology 27:209–228). Techniques to identify particular point mutations are well known to those skilled in the art.

B. Recovery, Culture and Transfection of HSC

Hematopoietic Stem Cells (HSC) are recovered from the peripheral blood or the bone marrow of the subject using any technique now known to those skilled in the art or to be developed. HSC can be conveniently obtained from a subject by apheresis according to techniques well known to those skilled in art. In one embodiment, the subject can be given Granulocyte-Colony Stimulating Factor for 3 days prior to and during 4 days of cell apheresis. The apheresed mononuclear cells are isolated by density gradient centrifugation or equivalent procedure, adherent cells are removed, and the HSC are isolated by anti-CD34 antibody. Commercially available columns sold under the trademarks CellPro and Isolex or their equivalents are suitable to practice the invention.

Patients with Sickle Cell Disease are susceptible to sickle cell crisis, which can be precipitated by the administration of G-CSF. Therefore, prior to initiation of the pre-apheresis crisis the subject should be given a prophylactic exchange transfusion.

Cells can be transfected with the CRV by any technique now known or to be developed for transfecting cells with DNA. Such techniques include electroporation, liposome transfer and calcium phosphate precipitation. In one embodiment the transfection is performed with a liposomal transfer compound, e.g., DOTAP (N-[1-(2,3-Dioleoyloxy) propyl]-N,N,N-trimethylammonium methylsulfate, Boehringer-Mannheim) or its equivalent. The amount of CRV is not critical to the practice of the invention; good results can be achieved with 10 nM/$10^5$ cells. A ratio of about 500 ng of CRV in 3 μg of DOTAP per $10^5$ cells can be used. The transfection technique of Examples 1–3, infra., can be used with the modification that the transfected cells are cultured in serum free media, media supplemented with human serum albumin or human serum.

In one embodiment of the invention, the apheresed HSC are transfected by exposure to a CRV and liposomal transfer compound mixture immediately after isolation and are allowed incubated for between from about 6 to 16 hours. The transfected cells are then washed to remove unabsorbed liposomes and cryopreserved according the techniques well known in the bone-marrow transplantation art. Cryopreservation is accomplished in culture medium containing 10% DMSO at a cooling rate of about 3° C./min.

C. Transplantation of the Repaired HSC

The repaired HSC can be transplanted into the subject using any of the techniques that are presently used for allotransplantation of HLA-matched bone marrow precursor cells in patients with sickle cell disease or with β-thalassemia. The subject undergoes a cytoreductive procedure immediately following the apheresis to obtain bone marrow cells. A dose of between 800 and 1200 Rads of total body irradiation can be used. Alternatively, bone marrow cytotoxic agents can be used. Any regime that can be used to prepare a subject for bone marrow implantation can be used. Regimes such as a combination of busulfan 3.5 mg/Kg/day, and cyclophosphamide 50 mg/kg/day each for 4 days prior to transplantation can be used. Alternatively, a dose of busulfan 4.0 mg/Kg/day with a lessor or no cyclophosphamide can be used to obtain significant if not complete ablation of the host bone marrow. The repaired HSC can be infused through a peripheral vein. The total dose of repaired, $CD34^+$cells to infused can be any dose that is effective to reconstitute the subjects bone marrow. Typically between about $1-4 \times 10^6$ $CD34^+$(HSC) cells/Kg are an effective dose.

Starting 48 hours after infusion of the repaired HSC recombinant Granulocyte-Colony Stimulating Factor (G-CSF) should be given in a dose of 10 μg/k/day, i.v., until the absolute neutrophil count reaches $1.5 \times 10^9$/L for three consecutive days. The art of bone marrow transplantation in thalassemia and Sickle Cell Disease is illustrated by Giardini, C., et al., 1995, Ann. Rev. Medicine 46:319–30; Abboud, M. R., 1994, American J. of Ped. Hematol./Oncol. 16:86–89; Storb, R., et al., 1991, Seminars in Hematology 28:235–39.

D. The Structure of the Chimeric Repair Vector

A Chimeric Repair Vector (CRV) is a 3',5'-linked nucleic acid, having at most one 3' and one 5' terminus, of between about 40 and about 100 nucleotides. In an alternative embodiment the 3' and 5' terminus can be covalently linked. When the 3' and 5' termini are not linked the CRV is said to be nicked. The CRV contains unpaired nucleotides, which form one or two hair-pin turns, which turn or turns divide(s) the CRV into two strands, so that at least 15 bases of the first strand are Watson-Crick paired to bases of the second strand. The CRV is further characterized by the presence of a plurality of segments of at least three contiguous bases comprised of 2'-O or 2'-alkylether ribose nucleotides which are Watson-Crick paired to deoxyribonucleotides of the second strand.

As used herein, the term "region" refers to a portion of a polynucleotide the sequence of which is derived from some particular source, e.g., a CRV having a region of at least 15 nucleotides having the sequence of a fragment of the human β-globin gene. A segment is a portion of a CRV having some structural significance. A given segment or a given region can contain both 2'-deoxynucleotides and ribonucleotides. However, a "ribonucleotide segment" or a "2'-deoxyribonucleotide segment" contain only ribo- and 2'-deoxyribonucleotides.

FIG. 1 shows the structure of one embodiment of CRV with segments (a)–(h). For the purposes of illustration the 3' terminus of the CRV is illustrated to be at the 3' end of the (a) segment and the 5' terminus is shown to be at the 5' end of the (h) segment, i.e., the nick is located at the boundary between (a) and (h) segments. However, the location of the nick, if any, and the orientation of 3' and 5' directions of the CRV with respect to the segments are not critical. The segments are labeled sequentially (a) through (h). In the embodiment of FIG. 1, a first region consists of segments (c), (d) and (e), which is complementary to a second region consisting of segment (a).

In one embodiment the lengths and characteristics of the segments are as follows. Segment (a) is between 16 and 40 nucleotides and preferably between 20 and 30 nucleotides. The sequence of the region of segment (a) can be either that of the coding strand or the non-coding strand of the normal, i.e., wild type, allele of the gene that contains the point mutation to be corrected (the "target gene"). As used herein, the statement that a region has a sequence of a fragment of the sequence of a particular gene means that it has the sequence derived from the coding strand of that gene, when the sequence of a segment or region is the same as the sequence of a fragment of either the coding or non-coding strand, the segment or region is said to be completely homologous to the gene. As used herein the sequence of the "wild-type" allele includes the sequence of any allele of the target gene that is not associated with the disease of the subject; thus, polymorphic genes have multiple wild-type sequences. The location of the sequence of segment (a) must include the portion of the target gene that contains the mutation to be repaired. Unless the target gene is not normally transcribed in target cell, it is preferred that the sequence of segment (a) is the sequence of the coding strand of the wild type target gene. When the target gene is not transcribed in the target cell, then neither the coding strand sequence or the non-coding strand sequence is preferred. The sequence of segment (a) determines the sequences and combined lengths of segments (c)–(e), which must be complementary to segment (a).

The nucleotides of the portion of segment (a) that are base paired with segments (c) and (e) can be any 2'-deoxyribonucleotide that is known or will be developed. The nucleotides of segments (c) and (e), which are termed ribonucleotide segments, can be any 2' O-ribonucleotides, i.e., nucleotides having 2'-hydroxyl or alkylether moieties. As used herein, the term "ribonucleotide" refers to any nucleotide having a 2'-O or 2'-alkylether. In a preferred embodiment, the nucleotides of segment (d), which is termed the intervening segment are 2'-deoxyribonucleotides. Alternatively, segment (d) can be made of ribonucleotides; when so made the boundaries between segments (c), (d) and (e) are not defined. Segments (b) and (f) through (h) can be of any type of nucleotide. The linking moieties between the nucleotides of the either deoxyribo-type or ribo-type can be phosphodiesters, phosphorothioates, phosphorodithioates or any other linkage group that permits the formation of duplex nucleic acids, allows for their transfection into cells and does not interfere with homologous recombination.

In a preferred embodiment, the sequence of segments (c) and (e) are completely homologous to the target gene. In a preferred embodiment, the sequence of segment (d) is completely homologous to a wild-type allele of the target gene; and is homologous to the target gene except for the targeted mutation or mutations.

Segments (b) and (g) are about 4 nucleotides in length and form single stranded hairpin turns that allow segments (a)

and (c)–(e) and segments (f) and (h) to form Watson-Crick base pairs, i.e., to form duplex nucleic acids.

Segments (c) and (e), also termed the first and second ribonucleotide segments, consist, in a preferred embodiment, of 2'-O-methylribonucleotides. In a preferred embodiment, segments (c) and (e) are independently, between 6 and 13 nucleotides.

Segment (d), also termed the intervening segment, in one embodiment, is between 4 and 20 nucleotides in length. Segment (d) must be homologous to the fragment of the target gene that includes the point mutation to be repaired, in which case the intervening segment is said to span the mutation. Preferably segment (d) includes nucleotides 3' and 5' to the point mutation, in which case the intervening segment is said to embrace the point mutation. If the target gene contains two or more point mutations that are separated by fewer than 15 nucleotides, each can be repaired by the same CRV.

Segments (f) and (h) form a duplex that brings the 3' and 5' ends of a CRV that is nicked between segments (a) and (h) into juxtaposition. The 3' and 5' termini can be, in one embodiment, dephosphorylated. In an alternative embodiment, the 3' and 5' termini can be covalently linked by a phosphodiester bond or equivalent, so that the CRV is a closed circular oligonucleotide. Segments (f) and (h) can be optionally deleted from a closed circular CRV.

E. Embodiments of the Invention Concerning Non-Hematopoietic Cells

The invention can be used to repair mutations or introduce mutations into any cell-type that can be removed from a subject's body, cultured and reimplanted into the subject. Techniques for the removal, culture and reimplantation of hepatocytes, in particular of hepatic reserve (stem) cells, have been described in patent publication WO94/08598 to Naughton, G. B. and Sibanda, B., Apr. 28, 1994. Genetic diseases that can be cured by repair of mutations in hepatocytes include: familial hypercholesteremia, caused by mutation in the LDL receptor; emphysema that caused by a mutation in the α1-antitrypsin gene; and hemophilia and Christmas Disease, which are caused by mutations in coagulation factors VIII and IX, respectively.

F. Specific Embodiments of the Invention

In one embodiment of the invention, the CRV is constructed so that the sequence of the CRV contains the sequence of a fragment of at least 15 nucleotides of the sequence of a normal allele of the human β-globin gene. The sequence of the most common allele of human β-globin is found at FIG. 2 of Lawn et al., 1980, CELL 21:647, which sequence is hereby incorporated by reference. CRV containing the sequence of a fragment of β-globin can be used to repair mutations causing sickle cell disease, HbC and β-thalassemia.

The embodiments suitable for repair of the HbC and Sickle cell mutations contain a sequence of a fragment of at least 15 nucleotides from the sequence: 5'-CAC CTG ACT CCT GAG GAG AAG TCT GCC-3' (SEQ ID NO:1). Embodiments suitable for the repair of the HbE mutation contain a sequence of a fragment of at least 15 nucleotides from the sequence: 5'-GAA GTT GGT GGT GAG GCC CTG GGC AGG-3' (SEQ ID NO:2). The nucleotides that are mutated in HbC, HbS and HbE are underlined.

In a second embodiment of the invention the CRV is constructed so that the sequence of the CRV contains the sequence of a fragment of at least 15 nucleotides of the sequence of a normal allele of the human glucocerebrosidase gene. The sequence of the most common allele of glucocerebrosidase is found at FIG. 2 Tsuji et al., 1986, J. Biol. Chem. 261:50–53, which sequence is hereby incorporated by reference.

Table I, below, contains a list of the more prevalent mutations found in Gaucher Disease and β-thalassemia; the location of the mutation and the sequence of a fragment of a wild-type allele that can be used in a CRV to repair the mutation. The sequences of Table I are the sequences of the coding strand given in the conventional 5' to 3' direction. The approximate location of the mutation is indicated by the underlined nucleotides.

EXAMPLES

Example 1.

The Use of CRV to Repair Episomal Alkaline Phosphatase

An expression plasmid containing the wild-type human liver/bone/kidney alkaline phosphatase cDNA under the control of the SV40 early promoter was obtained and designated pHAP. An identical plasmid with the mutant version of the cDNA was obtained and designated p711. The design of CRV to interconvert the sequences of pHAP and p711 are diagrammed in FIG. 2A. The CRV Ch1 was designed to repair the missense mutation at position 711. It has a G residue, the wild-type sequence, at the site corresponding to the mutation. Ch2 has a design identical to Ch1 except for an A instead of G at the site corresponding to position 711. Ch3 has the same sequence as Ch1 but the sequence of the ribonucleotide segments is that of the coding strand of the alkaline phosphate gene instead of the non-coding strand. The oligonucleotide Dh1 contained the same sequence as Ch1, but contained only 2'-deoxynucleotides.

The schematic of p711 in FIG. 2B shows the single point mutation, A, at position 711 in the coding region of the alkaline phosphatase cDNA, the SV40 early promoter ($P_E$), SV40 origin of replication (ori), polyadenylation addition site and small-t intron sequence for splicing (SV40 poly A). The dotted box in FIG. 2B indicates the sequence from pBR322 encoding the origin of replication and β-lactamase ($Amp^R$) gene. CHO cells were transfected with p711 and 6 h later the CRV, Ch1, was introduced to CHO cells previously transfected with p711. Both transfections were performed with lipofectin. The extent of the conversion to the wild-type phenotype was monitored at both biochemical and DNA sequence levels, by spectrophotometric measurement, histochemical staining and analysis of Hirt DNA.

Materials And Methods

Synthesis and purification of oligonucleotides: The chimeric oligonucleotides were synthesized on a 0.2 μmole scale using the 1000 Å wide pore CPG on the ABI 394 DNA/RNA synthesizer. THe exocyclic amine groups of DNA phosphoramidites (Applied Biosystems, Foster City, Calif.) are protected with benzoyl for adenine and cytidine and isobutyryl for guanine. The 2'-O-methyl RNA phosphoramidites (Glen Research, Sterling, Va.) are protected with phenoxyacetyl group for adenine, dimethylformamidine for guanine and isobutyryl for cytidine. After the synthesis was complete, the base-protecting groups were removed by heating in ethanol:concentrated ammonium hydroxide (1:3) for 20 h at 55° C. The crude oligonucleotide sample was mixed with 7M urea and 10% glycerol, heated to 70° C. and loaded on a 10% polyacrylamide gel containing 7M urea. After gel electrophoresis, DNA bands were visualized by UV shadowing, dissected from the gel, crushed and eluted overnight in TE buffer (10 mM Tris-HCl and 1 mM EDTA, pH 7.5) with shaking. The eluent containing gel pieces was spun through 0.45 µm spin filter (Millipore, Bedford, Mass.) and precipitated with ethanol. Samples were further desalted by G-25 spin column (Boehringer Mannheim, Indianapolis, Ind.) and greater than 95% of the purified oligonucleotides were found to be full length.

Transient Transfection and Histochemical Staining: CHO cells were maintained in DMEM (B.R.L., Bethesda, Md.) containing 10% FBS (B.R.L. Bethesda, Md.). Transient transfection was carried out by addition of 10 µg of lipofectin in 1 ml of OPTIMEM and added to each well. He alkaline phosphatase activity was measured 24 h after transfection of the oligonucleotide. For histochemical staining, the cells were washed with 0.15M NaCl three times, incubated with staining solution for 20 min and fixed with 50% ethanol. The staining solution consisted of 2 mg Fast Violet, 2 ml Naphtol AS-MX phosphate alkaline solution (Sigma Chemical Company, St. Louis, Mo.) in 50 ml of water.

Spectrophotometric Measurement of Alkaline Phosphate Activity: Transient transfection was carried out in triplicates by addition of 1 µg of the plasmid p711 with 1µg of lipofectin in 100 αl of OPTIMEM (B.R.L. Bethesda, Md.) to $1 \times 10^4$ CHO cells in a 96-well place. After 6 h, various amounts of Ch1 or other CRV were mixed with 1 µg of lipofectin in 100 µl of OPTIMEM and added to each well. After 18 h, the medium was aspirated and 200 µl of DMEM containing 10% FBS was added to each well. The alkaline phosphate activity was measured 24h after transfection of chimeric oligonucleotides. Spectrophotometric measurement was carried out by the Elisa Amplication System (B.R.L, Bethesda, Md.). Cells were washed with 0.15M NaCl three times and lysed in 100 µl of NP40 buffer containing 10 mM NaCl, 0.5% NP40, 3 mM MgCl2 and 10 mM Tris-HCl pH 7.5. A fraction of cell lysates (20 µl) was incubated with 50 µl of Elisa substrate and 50 µl of Elisa amplifier (B.R.L. Bethesda, Md.), the reaction was stopped by addition of 50 µl of 0.3 M $H_2SO_4$ after 5 min of incubation with amplifier. The extent of reaction was carried out within the linear range of the detection method. The absorbance was read by an Elisa Plate Reader (B.R.L. Bethesda, Md.) at a wavelength of 490 nm.

Hirt DNA Isolation, Colony Hybridization and Direct DNA Sequencing of PCR Fragment: The cells were harvested for vector DNA isolation by a modified alkaline lysis procedure 24 h after transfection with the chimeric oligonucleotide. The cells were detached by trypsinization, washed, and resuspended in 100 µl of a solution containing 50 mM Tris-HCl pH 8.0, 10 mM EDTA and 110 µl of a solution containing 50 mM Tri-HCl pH 8.0, 10 mM EDTA and 100 µg/ml of RNase A. An equal volume of cell lysis solution (0.2N NaOH and 1% SDS) was added, followed by 100 µl of neutralization solution (3M KAc, pH 5.5). A 10-min room temperature incubation was followed by centrifugation of 10,000 rpm for 10 min. The supernatant was extracted with an equal volume of phenol-chloroform and precipitated with ethanol. Hirt DNA was transformed into E. coli DH5α cells (B.R.L. Bethesda, Md.). Colonies from Hirt DNA were screened for specific hybridization for each probe designed to distinguish the point mutation. Colonies were grown on ampicillin plates, lifted onto nitrocellulose filter paper in duplicate, and processed for colony hybridization. The blots were hybridized to $^{32}$P-end-labelled oligonucleotide probes, 711-A (5'-CCGCCTACACCCACTCG-3' (SEQ ID NO:3)) or 711-G (5'-CCGCCTACGCCCACTCG-3' (SEQ ID NO:4)) at 37° C. in solution containing 5× Denhardts, 1% SDS, 2× SSC and 100 µg/ml denatured salmon sperm DNA.

Blots were washed at 52° C. in TMAC solution (3.0M tetramethylammonium chloride/50 mM Tris-HCl, pH 8.0, 2 mM EDTA and 0.1% SDS). Plasmid DNA was made from twenty colonies shown to hybridize to either 711-G or 711-A, using the Qiagen miniprep kit (Chatworth, Calif.). Several hundred bases flanking the 711 position of each plasmid were sequenced in both direction by automatic sequencing (ABI 373A, Applied Biosystem, Foster City, Calif.). A 190 bp PCR-amplified fragment was generated by $Vent_R$ polymerase (New England Biolabs, Beverly, Mass.) utilizing two primers (5'-CAATGTCCCTGATGTTATGCA-3' (SEQ ID NO:5) and 5'-CGCTGGGCCAAGGACGCT-3' (SEQ ID NO:6)), corresponding to position 630-650 and 803-822 of the alkaline phosphatase cDNA flanking the 711 position. The fragment was gel-purified and subjected to automatic DNA sequencing (ABI 373A, Applied Biosystem, Foster City, Calif.).

Oligonucleotide Stability Measurement: Ten ng of the $^{32}$P-end-labelled oligonucleotide was mixed with 500 ng of the unlabelled oligonucleotide and transfected as described above. In order to reduce a nonspecific binding of oligonucleotides, cells were washed extensively with PBS and a solution containing 1M NaCl/HAc pH 2.5. A crude lysate was prepared by lysing the cells in a solution containing 10 mM Tris-HCl pH 7.5, 0.5 mM $MgCl_2$ and 0.5% Triton x-100 followed by phenol-chloroform extraction. Lysates were analyzed by 15% polyacrylamide gel containing 7M urea followed by autoradiography. Oligonucleotides incubated in DMEM containing 10% FBS were processed and analyzed in the same manner.

In our experimental design, various chimeric oligonucleotides were introduced into CHO cells previously transfected with p711. The extent of the conversion to the wild-type phenotype was monitored by histochemical staining; red pigment was deposited on the cells expressing an active enzyme. When cells with he mutant gene were transfected with Ch1, red cells appeared at a frequency, of approximately one in three transfected CHO cells, on the average, at 11 nM. In contrast, neither Ch2 nor Dh1 caused an increased enzymatic activity. Conversion to wild-type was observed at a low level when cells were transfected with Ch3. The transfection frequency measured by the expression of the wild-type plasmid pHAP was estimated to be 30%.

The enzymatic activity was also measured by spectrophotometric method described above. A dose-dependent increase of alkaline phosphatase activity was observed up to 17 nM of Ch1 in the presence of p711 plasmid. The enzymatic activity of cells treated with Ch1 at 17 nM approached 60% of that observed from cells transfected with the wild-type plasmid, pHAP. The increase was sequence-specific since the same amount of Ch1 did not affect enzymatic activity of cells transfected with pHAP. Furthermore, Ch2 which contained a single base pair change from the Ch1 sequence did not cause any increase in enzymatic activity. The oligonucleotide, Dh1, which contained the same sequence as Ch1, but did not contain a ribonucleotide segment, did not exhibit an increase. Thus, spectrophotometric measurements of alkaline phosphatase activity were consistent with the result from the histochemical staining.

Correction of a Point Mutation of the Targeted DNA Sequence by the Chimeric Oligonucleotide: In order to confirm the change at the DNA sequence level, a Hirt extract was made from the cells transfected with the p711 and various oligonucleotides by a modified alkaline lysis procedure, Wang. G, et al., 1995, Mol. Cell. Biol. 15, 1759, 24 h after transfection of the chimeric oligonucleotide. Hirt DNA transformed DH5α cells efficiently, resulting in $10^4$ Amp$^R$ colonies from $10^6$ transfected CHO cells. DH5α transformants were screened for specific hybridization with a probe designed to distinguish between the point mutation (A) and the wild-type (G) sequence, corresponding to position 703–719 of mutant and normal cDNAs, respectively, Weiss, M. J., 2988, Proc. Natl. Acad. Sci. 85:7666. The frequency of correction was measured by averaging the number of colonies hybridized to the 711-G or 711-A probe using more than 500 colonies hybridized to the 711-G or 711-A probe using more than 500 colonies of the multiple plates generated from at least two separate transfection experiments (Table I). Similar frequencies of conversion were observed for two batches of Ch1 prepared by separate synthesis. Approximately 70% of the colonies generated from the Hirt DNA made from cells transfected with p711 and Ch1 hybridized to the 711-A probe, while 30% of colonies exhibited hybridization to the 711-G probe (Table I). Thus, a correction frequency of 30% was observed at 11 nM of Ch1, reproducibly. Hybridization was specific and no cross-hybridization was observed between the two populations. DNA sequencing was carried out with plasmid DNAs prepared from twenty of these colonies in both directions utilizing two primers (5'-CAATGTCCCTGATGTTATGCA-3' (SEQ ID NO:7) and 5'-CGCTGGGCCAAGGACGCT-3' (SEQ ID NO:8)), corresponding to position 630–650 and 803–822 of the alkaline phosphatase cDNA flanking the 711 position. The sequence conversion was confirmed in each case and no other alteration in sequence was observed within several hundred of bases surrounding the target nucleotide. All colonies from the Hirt extract prepared from Ch2 or Dh1-treated cells hybridized to the 711-A probe only (Table I). Some colonies from the Hirt extract of the Ch3 hybridized to the wild-type probe, but to a much lesser extent than that of the Ch1 (Table II). These results confirmed that the differential alkaline phosphatase activities exhibited were due to the correction of the point mutation (A to G) at the DNA sequence level.

RecA-deficient *E. coli* strains used to propagate plasmid DNA are capable of repair and homologous pairing functions using episomal DNA (21). In order to rule out the possibility that the sequence conversion is mediated by *E. coli*, direct DNA sequencing of a PCR-amplified fragment of Hirt DNA was carried out. Two primers flanking the 711 position were utilized to generate a 190 bp fragment through the action of Vent$_R$ polymerase. The results indicated that position 711 was a mixture of A(70%) and G(30%) when the Hirt DNA sample was made from the cells transfected cells with the combination of p711 and Ch1. In contrast, no mixed sequence was observed at position 711 when Hirt DNA was made from oligonucleotide Dh1. These results established clearly that sequence correction by the chimeric oligonucleotide occurred in mammalian cells.

Stability of Chimeric Oligonucleotide: The stability of the chimeric oligonucleotide was measured intracellularly and in growth medium containing 10% FBS. Ten nanogram of radiolabelled oligonucleotide, Ch1, was added to the same transfection experiment in which histochemical staining and Hirt DNA analyses was conducted (see Materials and Methods). The chimeric oligonucleotides are extremely stable. No detectable degradation was observed when chimeric oligonucleotide was incubated in growth medium containing 10% FBS, after 24 h incubation. Moreover, oligonucleotide isolated from cells did not exhibit any degradation during the same incubation time. Only monomers of the chimeric oligonucleotide were detected when isolate from cells 24 h after incubation. Thus, under the experimental conditions employed here, no end-to-end litigation of chimeric oligonucleotides was observed.

Example 2.

The Use of CRV to Repair the β-Globin Gene of an EB-Transformed Cell

A CRV to repair the mutation found in Sickle Cell Disease β-globin was designed SC1, FIG. 3. The molecule was composed of DNA residues with two intervening blocks of ten 2'-0-methyl RNA residues flanking a short stretch of five

TABLE II

Hybridization pattern of transformants from Hirt extract prepared from duplicate transfections of the p711 plasmid and various oligonucleotides at 11 nM.

| Oligo-nucleotide | Number of Transfections | Total number of colonies per plate | Number of colonies hybridizing to 711-G | Number of colonies hybridizing to 711-A | % Conversion |
|---|---|---|---|---|---|
| Ch1 | 1 | 84 | 32 | 54 | 38 |
| | | 189 | 70 | 117 | 37 |
| | | 219 | 74 | 143 | 34 |
| | 2 | 139 | 42 | 98 | 30 |
| | | 162 | 49 | 110 | 30 |
| | | 159 | 51 | 108 | 32 |
| Ch2 | 1 | 108 | 0 | 108 | 0 |
| | | 90 | 0 | 90 | 0 |
| | 2 | 218 | 0 | 218 | 0 |
| | | 148 | 0 | 148 | 0 |
| Ch3 | 1 | 190 | 3 | 185 | 2 |
| | | 151 | 4 | 145 | 3 |
| | 2 | 189 | 0 | 185 | 0 |
| | | 143 | 0 | 143 | 0 |
| Dh1 | 1 | 217 | 0 | 217 | 0 |
| | | 180 | 0 | 180 | 0 |
| | 2 | 157 | 0 | 157 | 0 |
| | | 188 | 0 | 188 | 0 |

DNA residues. When the molecule was folded into the duplex conformation, one strand contained only DNA residues while the other strand contained the RNA/DNA blocks. In this case, the internal sequence is complementary to the $\beta^S$ globin sequence over a stretch of 25 residues that span the site of the $\beta^S$ mutation, with the exception of a single base (T) which is in bold and designated with an asterisk. The five DNA residues flanked by RNA residues were centered about the mutant T residue in the $\beta^S$ coding sequence. A control chimeric oligonucleotide (SC2) was designed in the same manner with the exception of the base (A) designated in bold and with an asterisk. Genomic sequences of the $\beta^A$, $\beta^S$, and closely-related δ-globin genes are also displayed in FIG. 3A with the specific site of $\beta^S$ mutation printed in bold.

Lymphoblastoid cells were prepared as follows. Heparin-treated blood was obtained from discarded clinical material of a patient with sickle cell disease and from one of the investigators who had neither history nor symptoms of the disease. Mononuclear cells were prepared from blood (≈8 ml) by density gradient centrifugation in Ficoll and infected with Epstein-Barr virus which had been propagated in the marmoset cell line B95-8 (Coriell Institute for Medical Research #GM07404D). Infections were performed with addition of 0.1 mg leucoagglutinin PHA-L in 10 ml RPMI medium supplemented with 20% fetal bovine serum in a T25 flask. Cultures were fed twice a week starting on day 5 and were considered established once 60–70% of the cells remained viable at day 21. The $\beta^A$ and $\beta^S$ lymphoblastoid cells were maintained in RPMI medium containing 10% fetal bovine serum.

The CRV was introduced into the above-described lymphoblastoid cells homozygous for the $\beta^S$ allele as follows. Cells (1×105 per ml) were seeded in 1 ml of medium in each well of a 24-well tissue culture plate the day prior to the experiment. Transfections were performed by mixing chimeric oligonucleotides with 3 mg of DOTAP (N-[1-(2,3-Dioleoyloxy)propyl]-N,N,N-trimethylammonium methylsulfate, Boehringer-Mannheim) in 20 ml of 20 mM HEPES, pH 7.3, incubated at room temperature for 15 min, and added to the cultured cells. After 6 h the cells were harvested by centrifugation, washed and prepared for PCR amplification following the procedure of E. S. Kawasaki, PCR Protocols, Eds. M. A. Innis, D. H. Gelfand, J. J. Sninsky and T. J. White, pp146–152, Academic Press, (1990).

Correction of the single base mutation was assessed by taking advantage of well known restriction fragment length polymorphisms resulting from the $\beta^S$ mutation, R. F. Greeves et al., 1981, Proc. Natl. Acad. Sci. 78:5081; J. C. Chang and Y. W. Kan, 1982, N. Eng. J. Med. 307:30; S. H. Orkin et al., ibid., p. 32; J. T. Wilson et al., 1982, Proc. Natl. Acad. Sci. 79:3628. The A to T transversion in the $\beta^S$ allele results in the loss of a Bsu36I restriction site (CCTGAGG). Thus, the $\beta^S$ allele can be detected by Southern hybridization analysis of genomic DNA cut with Bsu36I. A 1.2 kbp Bsu36I DNA fragment of the β-globin gene present normally is absent in the $\beta^S$ allele and is replaced by a diagnostic 1.4 kbp fragment. When genomic DNA recovered from homozygous $\beta^S$ lymphoblastoid cells was analyzed by this procedure, the expected 1.4 kbp fragment was observed. However, two fragments were observed in DNA from cells transfected with the SC1 CRV. The presence of the 1.2 kbp fragment in addition to the 1.4 kbp fragment indicates partial correction of the $\beta^S$ allele had taken place in a dose-dependent fashion.

To measure the efficiency of correction rapidly and sensitively, we adapted a PCR-based RFLP analysis. For the analysis of the β-globin sequence, the 345 bp PCR fragment was prepared by amplification from a crude cell lysate using primers BG02 (5'-TCCTAAGCCAGTGCCAGAAGA-3' (SEQ ID NO:9)) and BG05 (5'-CTATTGGTCTC CTTAAACCTG-3' (SEQ ID NO:10)) and Expand Taq polymerase (Boehringer Mannheim). For the analysis of the δ-globin gene, the same cell extracts were used in amplification reactions with primers DG06 (5'-CTCACAAACTA ATGAAACCCTGC-3' (SEQ ID NO:11)) and DG07 (5'-GAAAACAGCCCAAGGGACAG-3' (SEQ ID NO:12)) to generate a 335 bp fragment. Gels were stained with SYBR# green (FMC Bioproducts) and fluorescence intensities were quantitated using a Molecular Dynamics fluoroimager. DNA sequencing was performed in both directions using an ABI 373A sequencer.

Figure 4A:
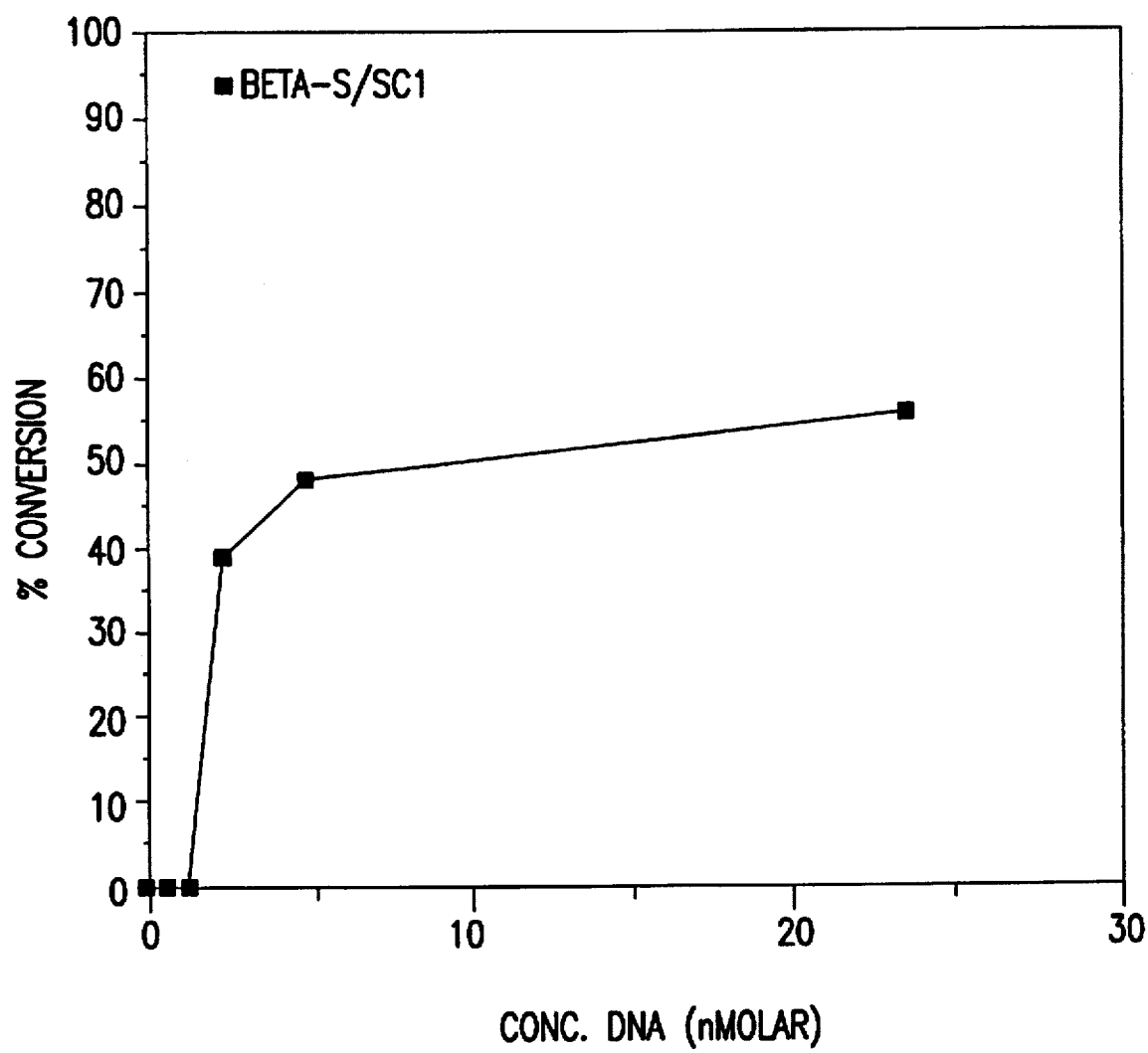
FIG. 4A and 4B.

The above primers were designed to yield a 345 bp fragment spanning the site of the $\beta^s$ mutation after PCR amplification of genomic DNA. The fragment from normal cells contained a Bsu36I recognition sequence and yielded fragments of 228 bp and 117 bp, while DNA from $\beta^s$ DNA contained the sequence CCTGTGG and remained refractory to cutting. Analysis indicated that the 345 bp DNA fragment amplified from SC1-treated $\beta^s$ cells was partially cleaved with Bsu36I, indicating correction of the mutation on some, but not all, chromosomes. A quantitative measure was obtained by comparing the relative intensities of the three DNA fragments after electrophoretic separation and staining with the fluorescent dye SYBR™ green. The stained bands were imaged using a laser fluorimager and the relative levels were calculated. Conversion efficiency was quantitated by scanning the cyber green-stained agarose gel with a fluoroimager. Experiments at doses of between 2.5 and 25.0 pM of SC1/10$^5$ $\beta^S$ lymphoblastoid cells showed between about 40% and 55% conversion of $\beta^S$ to $\beta^A$ (FIG. 4A).

Figure 4B:
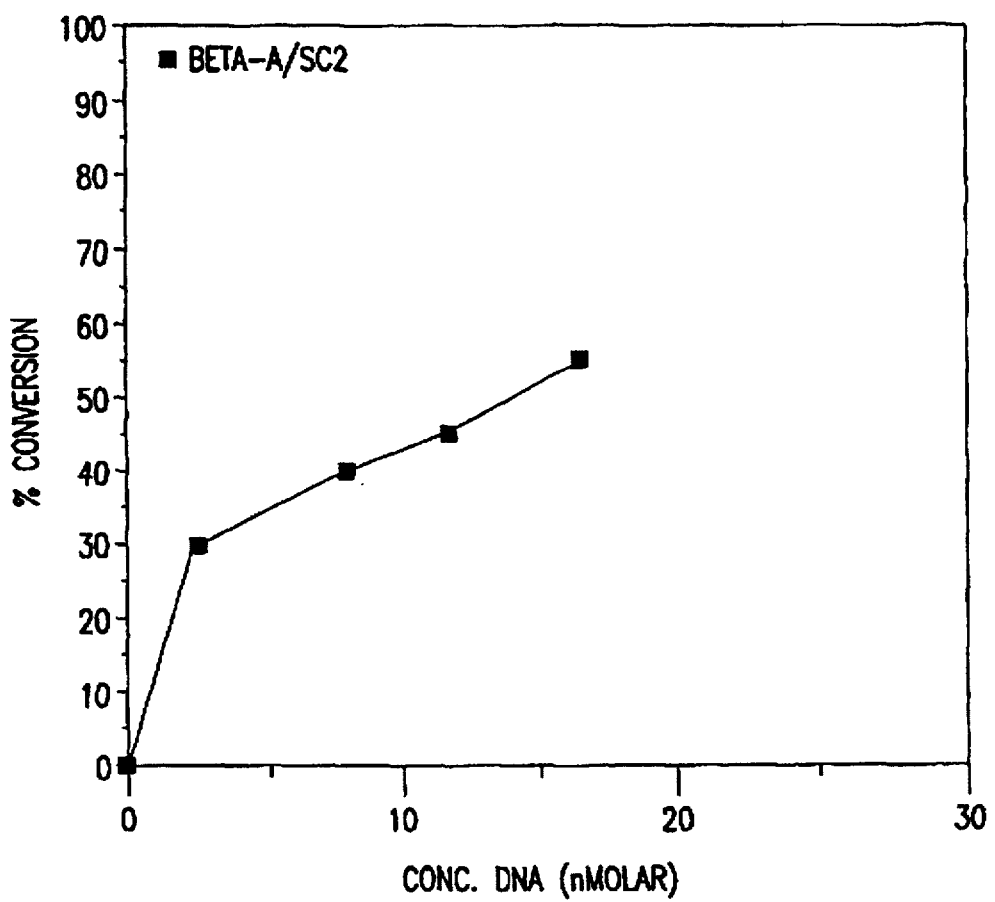

The frequency of introduction of the sickle mutation by the CRV SC2 was also determined by the methods set forth above. Analysis indicated that the level of correction exceeded 50% at the highest level of input chimeric molecule, 25 nM, but even at 2.5 nM correction of 30% of β-globin genes was observed (FIG. 4B).

Direct sequencing of the PCR amplified 345 bp fragment was performed to confirm the T to A change in the coding strand. In the DNA sample from $\beta^S$ cells transfected with chimeric molecule SC1 at a higher concentration greater than 12 nM/10$^5$ cells. Sequence analysis revealed an approximately equal mixture of A and T residues at the site of the $\beta^S$ mutation. DNA from untreated $\beta^S$ cells contained only T at that position and DNA from $\beta^A$ cells contained only A when treated with SC1. Treatment of $\beta^S$ cells transfected with the control CVR SC2 caused no change in the β-globin gene sequence. However, the DNA from normal cells transfected with SC2 was partially converted to the $\beta^S$ mutant sequence as evidenced by a mixture of T and A residues at the expected position of the sequence.

The specificity of the action of CVR was assessed by sequencing the related δ-globin gene, which is more than 90% homologous to the β-globin gene. The β and δ globin genes are identical over the 5 bp DNA core targeting region of SC1.

Two single base differences are underlined in FIG. 3. To determine whether SC2 altered the δ-globin gene, DNA sequence analysis was performed as above. The results showed that no alteration was introduced into the δ-globin gene by the SC2 CRV in contrast to the observed change directed by SC2 in the $\beta^A$-globin sequence.

Example 3.
The Experimental Use of CRV to Repair the β-Globin Gene of a HSC

Methods and Materials

Stem Cell Isolation and Transfection: Normal volunteers were given G-CSF 300 µg S.C. twice a day for five days. On the fourth and fifth days of G-CSF therapy they underwent a four hour stem cell apheresis using a COBE spectra pheresis machine. Mononuclear cells were prepared by density gradient centrifugation on Ficoll-Hypaque (density 1.077 g/ml, Pharmacia) (2000 rpm, 10 min, room temperature). The majority of the monocytes were removed after adherence to plastics (30 min, 37° C. in 5% $CO_2$ in RPMI with 10% FBS). Cells were harvested by swirling to remove cells loosely adherent to the plastics which were washed 3 times with PBS. This population was incubated with biotinylated murine anti-CD34 antibodies in PBS/1% BSA for 25 min at room temperature at a concentration of $100 \times 10^6$ cells/ml. The antibody-treated cells were passed over an avidin column and those passing through the column were then collected for analysis. Subsequently the column was washed with PBS and $CD34^+$ cells adhering to the column were recovered by squeezing the column. Final purities were assessed by FACS.

Cells were re-suspended in RPMI with 10% FCS heat inactivated and $1 \times 10^5$ cells/ml were plated in a 24 well pate with each well receiving $1 \times 10^5$ cells. The indicated amounts of chimeric oligonucleotide were mixed with 3 µg DOTAP in 20 µl of 20 mM HEPES, pH 7.3. The mixture was incubated on ice for 15 minutes then added to the cells. After 16 hr at 37° C., 5% $CO_2$, the cells were harvested, pelleted, washed with PBS and lysed with lysis buffer.

PCR Amplification and Analyses: Genomic DNA was amplified for PCR by using $PCO_2$ (5'-TCCTAAGCCAGT GCCAGAAGA-3' (SEQ ID NO:13)) and $PCO_5$(5'-CTATTGGTCTCCTTAAACCTG-3' (SEQ ID NO:14)) respectively and Expand Taq polymerase (Boehringer Mannheim, Indianapolis, Ind.) in a 50 µl reaction at 94° C. for 30 sec, 52.5° C. for 30 sec, 72° C. for 30 sec for 35 cycles to generate a 345 bp fragment. For the δ locus, the 5' primer was 5'-CTCACAAACCTAATG AAACCCTGC-3' (SEQ ID NO:15) and the 3' primer was 5'-GAAAACAGCCC AAGGGACAG-3' (SEQ ID NO:16) at 94° C. for 30 sec, 59° C. for 30 sec, 72° C. for 30 sec for 35 cycles.

The PCR product was digested with either Dde I or BSU36I restriction endonucleases (New England Biolabs, Beverly, Mass.) and loaded onto 1.2% agarose gel (1×TBE) and electrophoresed. The gel was stained for 20 min in 200 ml of 1×TBE containing 1:20,000 cyber green strain (FMC, Rockland, Me.) in the dark and quantitated by fluoroimager (Molecular Dynamics, Sunnyvale, Calif.). The PCR product was spun through a Qiaquick PCR purification spin column (Qiagen, Chatsworth, Calif.) in $H_2O$, dried down by vacuum to 5 µl and the concentration determined spectroscopically by O.D at 260 nm. The DNA samples (30 µg) were sequenced directly by an automated Applied Biosystems Model 373A DNA sequencing system (Applied Biosystems, Foster City, Calif.).

Synthesis and Purification of Oligonucleotides: The chimeric oligonucleotides were synthesized on a 0.2 µmole scale using the 1000 Å wide pore CPG on the ABI 394 DNA/RNA synthesizer. In this construct, the exocyclic amine groups of DNA phosphoramidites (Applied Biosystems) are protected with benzoyl for adenine and cytidine and isobutyryl for guanine. The 2'-O-methyl RNA phosphoramidites (Glen Research, Sterling, Va.) are protected with phenoxyacetyl group for adenine, dimethylformamidine for guanine and isobutyryl for cytidine. After synthesis, the base-protecting groups were removed by heating in ethanol: concentrated ammonium hydroxide (1:3) for 20 h at 550° C. The crude oligonucleotides were purified by polyacrylamide gel electrophoresis and the sample was mixed with 7M urea and 10% glycerol, heated to 70° C. and loaded on a 10% polyacrylamide gel containing 7M urea. After gel electrophoresis, DNA bands were visualized by UV shadowing, dissected from the gel, crushed and eluted overnight in TE buffer (10 mM Tris-HCl and 1 mM EDTA, pH 7.5) with shaking. The eluent containing gel pieces was spun through 0.45 Am spin filter (Millipore, Bedford, Mass.) and precipitated with ethanol. Samples were further desalted by G-25 spin column (Boehringer Mannheim) and greater than 95% of the purified oligonucleotides were found to be full length.

Results

The isolated $CD34^+$-enriched population was utilized first in an oligonucleotide uptake experiment. The chimeric molecule SC2 was mixed with the liposome formulation DOTAP under the conditions described above except that a radioactive tag was placed at the 5' end of the oligonucleotide. Increasing amounts of labeled and unlabeled oligonucleotide were incubated with the liposome for 15 minutes. The mixture was then incubated with cells for 6 hours after which the cells were washed extensively with PBS to reduce nonspecific binding. The cells were then centrifuged and the pellet fraction was washed with 0.2M glycine (pH 4.5) to eliminate any remaining nonspecific binding. The radioactivity in the cell pellet was determined by scintillation counting. The chimeric oligonucleotide was absorbed by the cell in dose-dependent fashion. Since our experimental strategy focused on nanomolar concentrations, we did not extend the curve beyond 25 nM. Based on the specific activity of the radiolabelled chimeric oligonucleotide and assuming that each cell is equally receptive to transformation, we estimate that up to approximately 50% of the $CD34^+$ cell population was transfected with the substrate. For each experiment, background levels were assessed by mixing radiolabelled chimeric molecules with the cells in the absence of DOTAP and this level never exceeded 0.05%.

A population of $CD34^+$-enriched cells containing two alleles with $\beta^A$ genotype were transfected with various amounts of SC2 and 3 µg/ml of DOTAP. Genomic DNA was isolated 16 h after transfection as described above and the extent of $\beta^A$ to $\beta^S$ conversion was measured by restriction enzyme polymorphism and by direct DNA sequencing. Genomic DNA isolated from $10^5$ cells was subjected to PCR amplification generating a 345 bp fragment by using the two primers $PCO_2$ and $PCO_5$. The $\beta^A$-specific sequence is cleaved by the restriction enzyme Dde I resulting in three fragments of 192, 108 and 45 base pairs, respectively, while the $\beta^S$-sequence would be cleaved only once, leaving a 300 bp and a 45 bp fragment. An increasing level of the uncut 300 bp fragment was observed as a function of increasing concentrations of SC2, indicating conversion of the $\beta^A$ to $\beta^S$ genotype, FIG. 5. A 50% frequency of conversion was observed at relatively low concentrations of chimeric oligonucleotide (600 ng =30 nM×1 ml). In contrast, no conversion was observed in cells treated with SC1, a chimeric molecule which pairs to the $\beta^A$ site with perfect complementarity.

Figure 5:
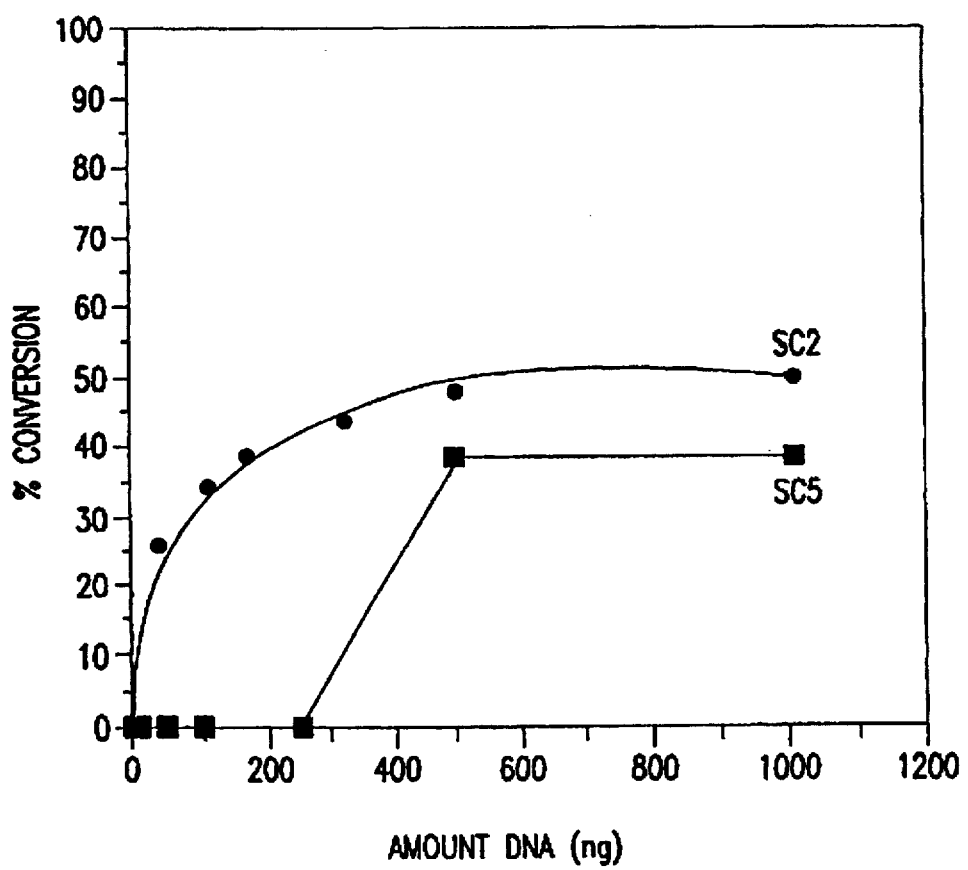
FIG. 5.

In order to confirm the DNA sequence change (A to T) in the normal cells, direct DNA sequencing of the 345 bp-fragment was carried out. The $CD34^+$population containing homozygous $\beta^A$ alleles was transfected with 23 nM SC2 as described. Genomic DNA was isolated, PCR-amplified and the samples subjected to automated DNA sequencing. The DNA sequence of β⁴ alone and β⁴ treated with the SC1 both contained T. In contrast, the DNA sequence of the β⁴ cells treated with the SC2 showed a dose-dependent conversion of T to A at the expected position. The SC2 CRV contains an (a) segment which is identical to the coding strand of the β-globin gene. The CRV designated SC5 contained an (a) segment identical to a fragment of the non-coding strand of the β-globin gene. We repeated the transfection experiments described above with SC2 and SC5. The results, presented in FIG. 5, show that SC5 was active, though not as active as SC2, and was apparently inactive at concentrations below 20 nM.

Genomic DNA from β⁴ cells that had been treated with SC2 was PCR-amplified utilizing the two δ-globin specific primers, PCO₆ and PCO₇. Only wild-type δ-globin sequence was found, which confirmed that the SC2 CRV is β-globin specific.

TABLE I

Beta Thalassemia

| Codon | Base Subst. | Affected Ethnic Group | Target Sequences (Affected sequences or codons have been underlined) | SEQ ID NO: |
|---|---|---|---|---|
| *Nonfunctional mRNA nonsense mutants* | | | | |
| 17 | A→T | Chin. | GCC CTG TGG GGC <u>AAG</u> GTG AAC GTG GAT | 17 |
| 39 | C→T | Med/Europe | TAC CCT TGG ACC <u>CAG</u> AGG TTC TTT GAG | 18 |
| 15 | G→A | Asian Indian | GTT ACT GCC CTG <u>TGG</u> GGC AAG GTG AAC | 19 |
| 121 | A→T | Polish/Swiss | CAC TTT GGC AAA <u>GAA</u> TTC ACC CCA CCA | 20 |
| 37 | G→A | Saudi | GTG GTC TAC CCT <u>TGG</u> ACC CAG AGG TTC | 21 |
| 43 | G→T | Chin. | CAG AGG TTC TTT <u>GAG</u> TCC TTT GGG GAT | 22 |
| 61 | A→T | Black | AAC CCT AAG GTG <u>AAG</u> GCT CAT GGC AAG | 23 |
| 35 | C→A | Thai | CTG CTG GTG GTC <u>TAC</u> CCT TGG ACC CAG | 24 |
| *Nonfunctional mRNA-frameshift mutants* | | | | |
| 1 | –G del | Med | ACA GAC ACC ATG <u>GTG</u> CAC CTG ACT CCT | 25 |
| 5 | –CT del | Med | GTG CAC CTG ACT <u>CCT</u> GAG GAG AAG TCY | 26 |
| 6 | –A del | Med | CAC CTG ACT CCT <u>GAG</u> GAG AAG TCY GCN | 27 |
| 8 | –AA del | Turk | ACT CCT GAG GAG <u>AAG</u> TCY GCN GTT ACT | 28 |
| 8/9 | +G ins | Asian Indian | ACT CCT GAG GAG <u>AAG</u> TCY GCN GTT ACT | 29 |
| 11 | –T del | Mexican | GAG AAG TCT GCC <u>GTT</u> ACT GCC CTG TGG | 30 |
| 14/15 | +G ins | Chin | GCC GTT ACT GCC <u>CTG TGG</u> GGC AAG GTG AAC | 31 |
| 16 | –C del | Asian Indian | ACT GCC CTG TGG <u>GGC</u> AAG GTG AAC GTG | 32 |
| 27–28 | +C ins | Chin | GTT GGT GGT GAG <u>GCC CTG</u> GGC AGG CTG CTG | 33 |
| 35 | –C del | Indonesian | CTG CTG GTG GTC <u>TAC</u> CCT TGG ACC CAG | 34 |
| 36–37 | –T del | Iranian | CTG GTG GTC TAC <u>CCT TGG</u> ACC CAG AGG TTC | 35 |
| 37 | –G del | Kurdish | GTG GTC TAC CCT <u>TGG</u> ACC CAG AGG TTC TTT | 36 |
| 41/42 | –CTTT del | As. Indian/Chin | TGG ACC CAG AGG <u>TTC TTT</u> GAG TCC TTT GGG | 37 |
| 44 | –C del | Kurdish | AGG TTC TTT GAG <u>TCC</u> TTT GGG GAT CTG | 38 |
| 47 | +A ins | Surinam. black | GAG TCC TTT GGG <u>GAT</u> CTG TCC ACT CCT | 39 |
| 64 | –G del | Swiss | GTG AAG GCT CAT <u>GGC</u> AAG AAA GTG CTC | 40 |
| 71 | +T ins | Chin | GTG CTC GGT GCC <u>TTT</u> AGT GAT GGC CTG | 41 |
| 71/72 | +A ins | Chin | GTG CTC GGT GCC <u>TTT AGT</u> GAT GGC CTG GCT | 42 |
| 76 | –C del | Italian | AGT GAT GGC CTG <u>GCT</u> CAC CTG GAC AAC | 43 |
| 82/83 | –G del | Azerbaijani | CTG GAC AAC CTC <u>AAG GGC</u> ACC TTT GCC ACA | 44 |
| 94 | +TG ins | Italian | GAG CTG CAC TGT <u>GAC</u> AAG CTG CAC GTG | 45 |
| 106/107 | +G ins | American black | AAC TTC AGG CTC <u>CTG GGC</u> AAC GTG CTG GTC | 46 |
| 109 | –G del | Lithuanian | CTC CTG GGC AAC <u>GTG CTG</u> GTC TGT GTG | 47 |
| 126 | –T del | Italian | TTC ACC CCA CCA <u>GTG</u> CAG GCN GCC TAT | 48 |
| *Initiator Codon Mutants* | | | | |
| ATG-AGG | | Chin | CAA ACA GAC ACC <u>ATG</u> GTG CAC CTG ACT | 49 |
| ATG-ACG | | Yugoslav | CAA ACA GAC ACC <u>ATG</u> GTG CAC CTG ACT | 50 |
| *RNA Processing Mutants-Splice junction changes* | | | | |
| IVS1 pos. 1 | G→A | Med | GAG GCC CTG GGC <u>AGG</u> TTG GTA TCA AGG | 51 |
| IVS1 pos. 1 | G→T | Asian Indian/Chinese | GAG GCC CTG GGC <u>AGG</u> TTG GTA TCA AGG | 52 |
| IVS2 pos. 1 | G→A | Med./Tunisian/Am. black | GAG AAC TTC AGG <u>GTG</u> AGT CTA TGG GAC | 53 |
| IVS1 pos. 2 | T→G | Tunisian | GCC CTG GGC AGG <u>TTG</u> GTA TCA AGG TTA | 54 |
| IVS1 pos. 2 | T→C | Black | GCC CTG GGC AGG <u>TTG</u> GTA TCA AGG TTA | 55 |
| IVS1 3' end | G→C | Italian | TTT CCC ACC CTT <u>AGG</u> CTG CTG GTG GTC | 56 |
| IVS2 3' end | A→G | American black | ATC TTC CTC CCA <u>CAG</u> CTC CTG GGC AAC | 57 |
| IVS2 3' end | A→C | American black | ATC TTC CTC CCA <u>CAG</u> CTC CTG GGC AAC | 58 |
| IVS1 3' end | G→A | Egyptian | TTT CCC ACC CTT <u>AGG</u> CTG CTG GTG GTC | 59 |
| *RNA Processing mutants-Consensus changes* | | | | |
| IVS1 pos. 5 | G→C | Asian Indian/Chin/Melanesian | CTG GGC AGG TTG <u>GTA</u> TCA AGG TTA CAA | 60 |
| IVS1 pos. 5 | G→T | Med./Black | CTG GGC AGG TTG <u>GTA</u> TCA AGG TTA CAA | 61 |
| IVS1 pos. 5 | G→A | Algerian | CTG GGC AGG TTG <u>GTA</u> TCA AGG TTA CAA | 62 |
| IVS1 pos. –1 (codon 30) | G→C | Tunisian/black | GAG GCC CTG GGC <u>AGG</u> TTG GTA TCA AGG | 63 |
| IVS1 pos. –1 (codon 30) | G→A | Bulgarian | GAG GCC CTG GGC <u>AGG</u> TTG GTA TCA AGG | 64 |
| IVS1 pos. –3 (codon 29) | C→T | Lebanese | GGT GAG GCC CTG <u>GGC</u> AGG TTG GTA TCA | 65 |
| IVS2 3' end | CAG→AAG | Iranian/Egyptian/Black | ATC TTC CTC CCA <u>CAG</u> CTC CTG GGC AAC GTG | 66 |

TABLE I-continued

| IVS1 3' end | TAG→GAG | Saudi Arabian | TAT TTT CCC ACC CT<u>T</u>AGG CTG CTG GTG GTC | 67 |

Internal IVS changes

| IVS1 pos. 110 | G→A | Med | TCT CTC TGC CTA <u>TTG</u> GTC TAT TTT CCC | 68 |
| IVS1 pos. 116 | T→G | Med | TGC CTA TTG GTC <u>TAT</u> TTT CCC ACC CTT | 69 |
| IVS2 pos. 705 | T→G | Med | AAA TTG TAA CTG <u>ATG</u> TAA GAG GTT TCA | 70 |
| IVS2 pos. 745 | C→G | Med 73 | AGC AGC TAC AAT CCA <u>GCT</u> ACC ATT CTG CTT | 71 |
| IVS2 pos. 654 | C→T | Chin 303 | TTT CTG GGT TAA <u>GGC</u> AAT AGC AAT ATT | 72 |

Coding region substitutions affecting processing

| 26 | G→A | SE Asian | GAA GTT GGT GGT <u>GAG</u> GCC CTG GGC AGG | 73 |
| 24 | T→A | Am. Black | GTG GAT GAA GTT <u>GGT</u> GGT GAG GCC CTG | 74 |
| 27 | G→T | Med | GTT GGT GGT GAG <u>GCC</u> CTG GGC AGG CTG | 75 |
| 19 | A→G | Malaysian | CTG TGG GGC AAG GTG <u>AAC</u> GTG GAT GAA GTT | 76 |

Gaucher Disease

| cDNA No. | Amino Acid No. | Genomic No. | Nucleotide Substitution | Amino Acid Substitution | Target Sequences (The Mutated Nucleotide is underlined) | SEQ ID NO: |
|---|---|---|---|---|---|---|

Common

| 1226 | 370 | 5841 | A→G | Asn→Ser | AGC ATC ATC ACG <u>A</u>AC CTC CTG TAC CAT | 77 |
| 1448 | 444 | 6433 | T→C | Leu→Pro | CAG AAG AAC GAC <u>C</u>TG GAC GCA GTG GCA | 78 |
| 84 | 1035 | | G→GG ins | | CCT AAA AGC TTC <u>GG</u>C TAC AGC TCG GTG | 79 |

Uncommon

| | IVS2 | 1067 | G→A | | TGT CGT GGG CAT CAG <u>G</u>TG AGT GAG TCA | 80 |
| 754 | 213 | 3548 | T→A | Phe→Ile | TGG GCC AGA TAC <u>T</u>TT GTG AAG TTC CTG | 81 |
| 1192 | 359 | 5408 | C→T | Arg→Stop | GGC TCC TGG GAT <u>C</u>GA GGG ATG CAG TAC | 82 |
| 1193 | 359 | 5409 | G→A | Arg→Gln | GGC TCC TGG GAT C<u>G</u>A GGG ATG CAG TAC | 83 |
| 1297 | 394 | 5912 | G→T | Val→Leu | GGA CCC AAT TGG <u>G</u>TG CGT AAC TTT GTC | 84 |
| 1342 | 409 | 5957 | G→C | Asp→His | GAC ATC ACC AAG <u>G</u>AC ACG TTT TAC AAA | 85 |
| 1504 | 463 | 6489 | C→T | Arg→Cys | GTC GTG CTA AAC <u>C</u>GC TCC TCT AAG GAT | 86 |
| 1604 | 496 | 6683 | G→A | Arg→His | TAC CTG TGG CGT C<u>G</u>C CAG TGA TGG AGC | 87 |

This information was adapted from The Metabolic and Molecular Bases of Inherited Disease, Charles R. Scriver, ed. (John B. Stanbury, James W. Wyngaarden, Donald S. Frederickson, Consulting Eds.) 7th Edition, McGraw-Hill, Health Professions Division, New York. 1995.

---

|---|---|

What is claimed is:

1. A nucleic acid, having at most one 3' end and one 5' end, comprising a segment of unpaired bases disposed so that the unpaired bases separate the nucleic acid into a first strand and a second strand, which first and second strands comprise a first region and a second region, respectively, each region having at least 15 nucleotides, in which:
   a) each nucleotide of the first region is Watson-Crick paired to a nucleotide of the second region;
   b) the first region comprises at least 8 ribonucleotides having other than a 2'-hydroxyl moiety, which are Watson-Crick paired to 2'-deoxynucleotides, which ribonucleotides form at least one ribonucleotide segment of at least 3 ribonucleotides; and
   c) the sequence of the first or the second region is the sequence of a fragment of a wild-type allele of a human gene.

2. The nucleic acid of claim 1, provided the human gene is other than ras.

3. The nucleic acid of claim 1, in which the sequence of the first or second region is 5'-AGC GCC GCC TAC GCC CAC TCG GCT GT-3' (nt 1–26 of SEQ ID NO: 88) or is a fragment thereof.

4. The nucleic acid of claim 2, provided the human gene is other than a gene encoding alkaline phosphatase.

5. The nucleic acid of claim 1, in which the first region is comprised of a first ribonucleotide segment of at least 6 contiguous ribonucleotides, a second ribonucleotide segment of at least 3 ribonucleotides, and an intervening segment disposed between the first and second ribonucleotide segments, which intervening segment comprises at least three 2'-deoxyribonucleotides.

6. The nucleic acid of claim 4, in which the second region comprises between about 20 and about 100 2'-deoxyribonucleotides.

7. The nucleic acid of claim 5, in which the first and second ribonucleotide segments each consist of between about 6 and about 13 ribonucleotides and the intervening segment consists of between about 4 and about 20 2'-deoxyribonucleotides.

8. The nucleic acid of claim 5, in which the first and second ribonucleotide segments each consist of between about 8 and about 12 ribonucleotides and the intervening segment consists of between about 4 and about 15 2'-deoxyribonucleotides.

9. The nucleic acid of claim 5, in which the first and second ribonucleotide segments each consist of about 10 ribonucleotides and the intervening segment consists of about 5 2'-deoxyribonucleotides.

10. The nucleic acid of claim 3, in which the human gene is selected from the group consisting of a β-globin gene and a glucocerebrosidase gene.

11. The nucleic acid of claim 9, in which the sequence of the first or second region is selected from the sequences of Table I or is a fragment thereof.

12. The nucleic acid of claim 9, in which the sequence of the first or second region is 5'-CAC CTG ACT CCT GAG GAG AAG TCT GCC-3' (SEQ ID NO: 99) or 5'-GAA GTT GGT GGT GAG GCC CTG GGC AGG-3' (SEQ ID NO: 100) or a fragment thereof.

13. A method of repairing a mutation of a cell of a human subject, which comprises removing a cell from a subject, having a disease caused by the presence of a CRV-repairable mutation in the cell, and introducing a nucleic acid into the removed cell, wherein said nucleic acid has at most one 3' end and one 5' end and comprises a segment of unpaired bases disposed so that the unpaired bases separate the nucleic acid into a first strand and a second strand, which first and second strands comprise a first region and a second region, respectively, each region having at least 15 nucleotides, in which:
   a) each nucleotide of the first region is Watson-Crick paired to a nucleotide of the second region;
   b) the first region comprises at least 8 ribonucleotides having other than a 2'-hydroxyl moiety, which are Watson-Crick paired to 2'-deoxynucleotides, which ribonucleotides form at least one segment of at least 3 contiguous ribonucleotides; and
   c) the sequence of the first or the second region is the sequence of a fragment of a wild-type allele of a human gene, which fragment embraces the CRV-repairable mutation, whereby the mutation in the cell is replaced by the wild-type allele.

14. The method of claim 12, in which the sequence of the first or second region is 5'-AGC GCC GCC TAC GCC CAC TCG GCT GT-3' (nt 1–26 of SEQ ID NO: 88) or is a fragment thereof.

15. The method of claim 12, which further comprises the step of reimplanting the repaired cell into the subject.

16. The method of claim 13, wherein the first region of the nucleic acid is comprised of a first ribonucleotide segment of at least 6 contiguous ribonucleotides, a second ribonucleotide segment, and an intervening segment disposed between the first and second ribonucleotide segments, which intervening segment comprises at least three 2'-deoxyribonucleotides and wherein the cell is a hematopoietic stem cell.

17. The method of claim 14, in which the intervening segment embraces the CVR-repairable mutation.

18. The method of claim 14, in which the human gene selected from the group consisting of a β-globin gene and a glucocerebrosidase gene.

19. The method of claim 16, in which the sequence of the first or second region is selected from the sequences of Table I or is a fragment thereof.

20. The method of claim 16, in which the sequence of the first or second region is 5'-CAC CTG ACT CCT GAG GAG AAG TCT GCC-3' (SEQ ID NO: 99) or 5'-GAA GTT GGT GGT GAG GCC CTG GGC AGG-3' (SEQ ID NO: 100) or is a fragment thereof.

21. A method of repairing a mutation in a hepatocyte of a human subject, which comprises removing a hepatocyte from a subject, having a disease caused by the presence of a CRV-repairable mutation in the hepatocyte, and introducing a nucleic acid into the removed cell, wherein said nucleic acid has at most one 3' end and one 5' end and comprises a segment of unpaired bases disposed so that the unpaired bases separate the nucleic acid into a first strand and a second strand, which first and second strands comprise a first region and a second region, respectively, each region having at least 15 nucleotides, in which:
 a) each nucleotide of the first region is Watson-Crick paired to a nucleotide of the second region;
 b) the first region comprises at least 8 ribonucleotides having other than a 2'-hydroxyl moiety, which are Watson-Crick paired to 2'-deoxynucleotides, which ribonucleotides form a first ribonucleotide segment of at least 6 contiguous ribonucleotides, and a second ribonucleotide segment of at least 6 contiguous ribonucleotides;
 c) the first region further comprises an intervening segment of at least 3 deoxyribonucleotides disposed between the first and second ribonucleotide segments; and
 d) the sequence of the first or the second region is the sequence of a fragment of a wild-type allele of a human gene and the intervening segment embraces the CRV-repairable mutation, whereby the mutation in the cell is replaced by the wild-type allele.

22. The method of claim 21, wherein the nucleic acid comprises at least eight 2'-alkylether substituted ribonucleotides.

23. The method of claim 16, wherein the nucleic acid comprises at least eight 2'-alkylether substituted ribonucleotides.

24. The method of claim 13, wherein the nucleic acid comprises at least eight 2'-alkylether substituted ribonucleotides.

25. The nucleic acid of claim 5, which comprises at least eight 2'-alkylether substituted ribonucleotides.

* * * * *

SEQUENCE LISTING ( 1 ) GENERAL INFORMATION:

( i i i ) NUMBER OF SEQUENCES: 100

( 2 ) INFORMATION FOR SEQ ID NO:1:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:1:

CACCTGACTC CTGAGGAGAA GTCTGCC        27

( 2 ) INFORMATION FOR SEQ ID NO:2:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

GAAGTTGGTG GTGAGGCCCT GGGCAGG        27

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CCGCCTACAC CCACTCG                                          17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CCGCCTACGC CCACTCG                                          17

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

CAATGTCCCT GATGTTATGC A                                 21

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CGCTGGGCCA AGGACGCT                                        18

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CAATGTCCCT GATGTTATGC A                                 21

( 2 ) INFORMATION FOR SEQ ID NO:8:

( i ) SEQUENCE CHARACTERISTICS:
        ( A ) LENGTH: 18 base pairs
        ( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:8:

CGCTGGGCCA AGGACGCT 18

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:9:

TCCTAAGCCA GTGCCAGAAG A 21

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:10:

CTATTGGTCT CCTTAAACCT G 21

( 2 ) INFORMATION FOR SEQ ID NO:11:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:11:

CTCACAAACT AATGAAACCC TGC 23

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:12:

GAAAACAGCC CAAGGGACAG 20

( 2 ) INFORMATION FOR SEQ ID NO:13:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:13:

TCCTAAGCCA GTGCCAGAAG A                    21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CTATTGGTCT CCTTAAACCT G                    21

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CTCACAAACC TAATGAAACC CTGC                 24

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GAAAACAGCC CAAGGGACAG                      20

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:17:

GCCCTGTGGG GCAAGGTGAA CGTGGAT              27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:18:

TACCCTTGGA CCCAGAGGTT CTTTGAG              27

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:19:

GTTACTGCCC TGTGGGGCAA GGTGAAC       27

( 2 ) INFORMATION FOR SEQ ID NO:20:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:20:

CACTTTGGCA AAGAATTCAC CCCACCA       27

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:21:

GTGGTCTACC CTTGGACCCA GAGGTTC       27

( 2 ) INFORMATION FOR SEQ ID NO:22:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:22:

CAGAGGTTCT TTGAGTCCTT TGGGGAT       27

( 2 ) INFORMATION FOR SEQ ID NO:23:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:23:

AACCCTAAGG TGAAGGCTCA TGGCAAG       27

( 2 ) INFORMATION FOR SEQ ID NO:24:

( i ) SEQUENCE CHARACTERISTICS:
        ( A ) LENGTH: 27 base pairs
        ( B ) TYPE: nucleic acid (C) STRANDEDNESS: single
(D) TOPOLOGY: unknown (i i) MOLECULE TYPE: DNA (genomic)

(x i) SEQUENCE DESCRIPTION: SEQ ID NO:24:

CTGCTGGTGG TCTACCCTTG GACCCAG  27

(2) INFORMATION FOR SEQ ID NO:25:

(i) SEQUENCE CHARACTERISTICS:
(A) LENGTH: 27 base pairs
(B) TYPE: nucleic acid
(C) STRANDEDNESS: single
(D) TOPOLOGY: unknown (i i) MOLECULE TYPE: DNA (genomic)

(x i) SEQUENCE DESCRIPTION: SEQ ID NO:25:

ACAGACACCA TGGTGCACCT GACTCCT  27

(2) INFORMATION FOR SEQ ID NO:26:

(i) SEQUENCE CHARACTERISTICS:
(A) LENGTH: 27 base pairs
(B) TYPE: nucleic acid
(C) STRANDEDNESS: single
(D) TOPOLOGY: unknown (i i) MOLECULE TYPE: DNA (genomic)

(x i) SEQUENCE DESCRIPTION: SEQ ID NO:26:

GTGCACCTGA CTCCTGAGGA GAAGTCY  27

(2) INFORMATION FOR SEQ ID NO:27:

(i) SEQUENCE CHARACTERISTICS:
(A) LENGTH: 27 base pairs
(B) TYPE: nucleic acid
(C) STRANDEDNESS: single
(D) TOPOLOGY: unknown (i i) MOLECULE TYPE: DNA (genomic)

(x i) SEQUENCE DESCRIPTION: SEQ ID NO:27:

CACCTGACTC CTGAGGAGAA GTCYGCN  27

(2) INFORMATION FOR SEQ ID NO:28:

(i) SEQUENCE CHARACTERISTICS:
(A) LENGTH: 27 base pairs
(B) TYPE: nucleic acid
(C) STRANDEDNESS: single
(D) TOPOLOGY: unknown (i i) MOLECULE TYPE: DNA (genomic)

(x i) SEQUENCE DESCRIPTION: SEQ ID NO:28:

ACTCCTGAGG AGAAGTCYGC NGTTACT  27

(2) INFORMATION FOR SEQ ID NO:29:

(i) SEQUENCE CHARACTERISTICS:
(A) LENGTH: 27 base pairs
(B) TYPE: nucleic acid
(C) STRANDEDNESS: single
(D) TOPOLOGY: unknown (i i) MOLECULE TYPE: DNA (genomic)

( x i ) SEQUENCE DESCRIPTION: SEQ ID NO:29:

ACTCCTGAGG AGAAGTCYGC NGTTACT  27

( 2 ) INFORMATION FOR SEQ ID NO:30:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:30:

GAGAAGTCTG CCGTTACTGC CCTGTGG  27

( 2 ) INFORMATION FOR SEQ ID NO:31:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:31:

GCCGTTACTG CCCTGTGGGG CAAGGTGAAC  30

( 2 ) INFORMATION FOR SEQ ID NO:32:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:32:

ACTGCCCTGT GGGGCAAGGT GAACGTG  27

( 2 ) INFORMATION FOR SEQ ID NO:33:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:33:

GTTGGTGGTG AGGCCCTGGG CAGGCTGCTG  30

( 2 ) INFORMATION FOR SEQ ID NO:34:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: unknown ( i i ) MOLECULE TYPE: DNA (genomic)

( x i ) SEQUENCE DESCRIPTION: SEQ ID NO:34:

CTGCTGGTGG TCTACCCTTG GACCCAG  27

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:35:

```
CTGGTGGTCT ACCCTTGGAC CCAGAGGTTC                                      30
```

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:36:

```
GTGGTCTACC CTTGGACCCA GAGGTTCTTT                                      30
```

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:37:

```
TGGACCCAGA GGTTCTTTGA GTCCTTTGGG                                      30
```

( 2 ) INFORMATION FOR SEQ ID NO:38:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:38:

```
AGGTTCTTTG AGTCCTTTGG GGATCTG                                         27
```

( 2 ) INFORMATION FOR SEQ ID NO:39:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:39:

```
GAGTCCTTTG GGGATCTGTC CACTCCT                                         27
```

( 2 ) INFORMATION FOR SEQ ID NO:40:

( i ) SEQUENCE CHARACTERISTICS:
        ( A ) LENGTH: 27 base pairs
        ( B ) TYPE: nucleic acid (C) STRANDEDNESS: single
    (D) TOPOLOGY: unknown (ii) MOLECULE TYPE: DNA (genomic)

(xi) SEQUENCE DESCRIPTION: SEQ ID NO:40:

GTGAAGGCTC ATGGCAAGAA AGTGCTC         27

(2) INFORMATION FOR SEQ ID NO:41:

(i) SEQUENCE CHARACTERISTICS:
    (A) LENGTH: 27 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:41:

GTGCTCGGTG CCTTTAGTGA TGGCCTG         27

(2) INFORMATION FOR SEQ ID NO:42:

(i) SEQUENCE CHARACTERISTICS:
    (A) LENGTH: 30 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:42:

GTGCTCGGTG CCTTTAGTGA TGGCCTGGCT      30

(2) INFORMATION FOR SEQ ID NO:43:

(i) SEQUENCE CHARACTERISTICS:
    (A) LENGTH: 27 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:43:

AGTGATGGCC TGGCTCACCT GGACAAC         27

(2) INFORMATION FOR SEQ ID NO:44:

(i) SEQUENCE CHARACTERISTICS:
    (A) LENGTH: 30 base pairs
    (B) TYPE: nucleic acid
    (C) STRANDEDNESS: single
    (D) TOPOLOGY: unknown (ii) MOLECULE TYPE: DNA (genomic)

(xi) SEQUENCE DESCRIPTION: SEQ ID NO:44:

CTGGACAACC TCAAGGGCAC CTTTGCCACA      30

(2) INFORMATION FOR SEQ ID NO:45:

(i) SEQUENCE CHARACTERISTICS:
    (A) LENGTH: 27 base pairs
    (B) TYPE: nucleic acid
    (C) STRANDEDNESS: single
    (D) TOPOLOGY: unknown (ii) MOLECULE TYPE: DNA (genomic)

(x i) SEQUENCE DESCRIPTION: SEQ ID NO:45:

GAGCTGCACT GTGACAAGCT GCACGTG 27

(2) INFORMATION FOR SEQ ID NO:46:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:46:

AACTTCAGGC TCCTGGGCAA CGTGCTGGTC 30

(2) INFORMATION FOR SEQ ID NO:47:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:47:

CTCCTGGGCA ACGTGCTGGT CTGTGTG 27

(2) INFORMATION FOR SEQ ID NO:48:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:48:

TTCACCCCAC CAGTGCAGGC NGCCTAT 27

(2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:49:

CAAACAGACA CCATGGTGCA CCTGACT 27

(2) INFORMATION FOR SEQ ID NO:50:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (i i) MOLECULE TYPE: DNA (genomic)

(x i) SEQUENCE DESCRIPTION: SEQ ID NO:50:

CAAACAGACA CCATGGTGCA CCTGACT 27

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:51:

GAGGCCCTGG GCAGGTTGGT ATCAAGG                                                  27

( 2 ) INFORMATION FOR SEQ ID NO:52:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:52:

GAGGCCCTGG GCAGGTTGGT ATCAAGG                                                  27

( 2 ) INFORMATION FOR SEQ ID NO:53:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:53:

GAGAACTTCA GGGTGAGTCT ATGGGAC                                                 27

( 2 ) INFORMATION FOR SEQ ID NO:54:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:54:

GCCCTGGGCA GGTTGGTATC AAGGTTA                                                 27

( 2 ) INFORMATION FOR SEQ ID NO:55:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:55:

GCCCTGGGCA GGTTGGTATC AAGGTTA                                                 27

( 2 ) INFORMATION FOR SEQ ID NO:56:

( i ) SEQUENCE CHARACTERISTICS:
        ( A ) LENGTH: 27 base pairs
        ( B ) TYPE: nucleic acid ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:56:

TTTCCCACCC TTAGGCTGCT GGTGGTC 27

( 2 ) INFORMATION FOR SEQ ID NO:57:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:57:

ATCTTCCTCC CACAGCTCCT GGGCAAC 27

( 2 ) INFORMATION FOR SEQ ID NO:58:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:58:

ATCTTCCTCC CACAGCTCCT GGGCAAC 27

( 2 ) INFORMATION FOR SEQ ID NO:59:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:59:

TTTCCCACCC TTAGGCTGCT GGTGGTC 27

( 2 ) INFORMATION FOR SEQ ID NO:60:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:60:

CTGGGCAGGT TGGTATCAAG GTTACAA 27

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:61:

CTGGGCAGGT TGGTATCAAG GTTACAA 27

( 2 ) INFORMATION FOR SEQ ID NO:62:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:62:

CTGGGCAGGT TGGTATCAAG GTTACAA 27

( 2 ) INFORMATION FOR SEQ ID NO:63:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:63:

GAGGCCCTGG GCAGGTTGGT ATCAAGG 27

( 2 ) INFORMATION FOR SEQ ID NO:64:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:64:

GAGGCCCTGG GCAGGTTGGT ATCAAGG 27

( 2 ) INFORMATION FOR SEQ ID NO:65:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:65:

GGTGAGGCCC TGGGCAGGTT GGTATCA 27

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:66:

ATCTTCCTCC CACAGCTCCT GGGCAACGTG 30

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:67:

TATTTTCCCA CCCTTAGGCT GCTGGTGGTC       30

( 2 ) INFORMATION FOR SEQ ID NO:68:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:68:

TCTCTCTGCC TATTGGTCTA TTTTCCC       27

( 2 ) INFORMATION FOR SEQ ID NO:69:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:69:

TGCCTATTGG TCTATTTTCC CACCCTT       27

( 2 ) INFORMATION FOR SEQ ID NO:70:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:70:

AAATTGTAAC TGATGTAAGA GGTTTCA       27

( 2 ) INFORMATION FOR SEQ ID NO:71:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:71:

AGCAGCTACA ATCCAGCTAC CATTCTGCTT       30

( 2 ) INFORMATION FOR SEQ ID NO:72:

( i ) SEQUENCE CHARACTERISTICS:
        ( A ) LENGTH: 27 base pairs
        ( B ) TYPE: nucleic acid (C) STRANDEDNESS: single
        (D) TOPOLOGY: unknown (ii) MOLECULE TYPE: DNA (genomic)

(xi) SEQUENCE DESCRIPTION: SEQ ID NO:72:

TTTCTGGGTT AAGGCAATAG CAATATT 27

(2) INFORMATION FOR SEQ ID NO:73:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:73:

GAAGTTGGTG GTGAGGCCCT GGGCAGG 27

(2) INFORMATION FOR SEQ ID NO:74:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:74:

GTGGATGAAG TTGGTGGTGA GGCCCTG 27

(2) INFORMATION FOR SEQ ID NO:75:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:75:

GTTGGTGGTG AGGCCCTGGG CAGGCTG 27

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:76:

CTGTGGGGCA AGGTGAACGT GGATGAAGTT 30

(2) INFORMATION FOR SEQ ID NO:77:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: DNA (genomic)

( x i ) SEQUENCE DESCRIPTION: SEQ ID NO:77:

AGCATCATCA CGAACCTCCT GTACCAT                27

( 2 ) INFORMATION FOR SEQ ID NO:78:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:78:

CAGAAGAACG ACCTGGACGC AGTGGCA                27

( 2 ) INFORMATION FOR SEQ ID NO:79:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:79:

CCTAAAAGCT TCGGCTACAG CTCGGTG                27

( 2 ) INFORMATION FOR SEQ ID NO:80:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:80:

TGTCGTGGGC ATCAGGTGAG TGAGTCA                27

( 2 ) INFORMATION FOR SEQ ID NO:81:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:81:

TGGGCCAGAT ACTTTGTGAA GTTCCTG                27

( 2 ) INFORMATION FOR SEQ ID NO:82:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:82:

GGCTCCTGGG ATCGAGGGAT GCAGTAC                27

( 2 ) INFORMATION FOR SEQ ID NO:83:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:83:

GGCTCCTGGG ATCGAGGGAT GCAGTAC                                      27

( 2 ) INFORMATION FOR SEQ ID NO:84:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:84:

GGACCCAATT GGGTGCGTAA CTTTGTC                                      27

( 2 ) INFORMATION FOR SEQ ID NO:85:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:85:

GACATCACCA AGGACACGTT TTACAAA                                      27

( 2 ) INFORMATION FOR SEQ ID NO:86:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:86:

GTCGTGCTAA ACCGCTCCTC TAAGGAT                                      27

( 2 ) INFORMATION FOR SEQ ID NO:87:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:87:

TACCTGTGGC GTCGCCAGTG ATGGAGC                                      27

( 2 ) INFORMATION FOR SEQ ID NO:88:

( i ) SEQUENCE CHARACTERISTICS:
        ( A ) LENGTH: 68 base pairs
        ( B ) TYPE: nucleic acid ( C ) STRANDEDNESS: single
( D ) TOPOLOGY: linear ( i i ) MOLECULE TYPE: DNA ( i x ) FEATURE:
  ( A ) NAME/KEY: Cb1
  ( B ) LOCATION: 1...68
  ( D ) OTHER INFORMATION:

( x i ) SEQUENCE DESCRIPTION: SEQ ID NO:88:

```
AGCGCCGCCT ACGCCCACTC GGCTGTTTTC AGCAGCGUGG GCGTAGGCGG CGCUGCGCGT    60
TTTCGCGC                                                             68
```

( 2 ) INFORMATION FOR SEQ ID NO:89:

( i ) SEQUENCE CHARACTERISTICS:
  ( A ) LENGTH: 68 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Cb2
  ( B ) LOCATION: 1...68
  ( D ) OTHER INFORMATION:

( x i ) SEQUENCE DESCRIPTION: SEQ ID NO:89:

```
AGCGCCGCCT ACACCCACTC GGCTGTTTTC AGCCGAGUGG GTGTAGGCGG CGCUGCGCGT    60
TTTCGCGC                                                             68
```

( 2 ) INFORMATION FOR SEQ ID NO:90:

( i ) SEQUENCE CHARACTERISTICS:
  ( A ) LENGTH: 68 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Cb3
  ( B ) LOCATION: 1...68
  ( D ) OTHER INFORMATION:

( x i ) SEQUENCE DESCRIPTION: SEQ ID NO:90:

```
GCGCGTTTTC GCGCAGCGCC GCCUACGCCC ACUCGGCUGT TTTCAGCCGA GTGGGCGTAG    60
GCGGCGCT                                                             68
```

( 2 ) INFORMATION FOR SEQ ID NO:91:

( i ) SEQUENCE CHARACTERISTICS:
  ( A ) LENGTH: 68 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Dh1
  ( B ) LOCATION: 1...68
  ( D ) OTHER INFORMATION:

( x i ) SEQUENCE DESCRIPTION: SEQ ID NO:91:

```
AGCGCCGCCT ACGCCCACTC GGCTGTTTTC AGCCGAGTGG GCGTAGGCGG CGCTGCGCGT    60
```

TTTCGCGC                                                                                    68

(2) INFORMATION FOR SEQ ID NO:92:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:92:

ACCCCCAGCG CCGCCTACAC CCACTCGGCT GACCGG                                                      36

(2) INFORMATION FOR SEQ ID NO:93:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: SC1
        (B) LOCATION: 1...68
        (D) OTHER INFORMATION:

(xi) SEQUENCE DESCRIPTION: SEQ ID NO:93:

ACCTGACTCC TGAGGAGAAG TCTGCTTTTG CAGACUUCUC CTCAGGAGUC AGGUGCGCGT    60

TTTCGCGC                                                                                    68

(2) INFORMATION FOR SEQ ID NO:94:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: SC2
        (B) LOCATION: 1...68
        (D) OTHER INFORMATION:

(xi) SEQUENCE DESCRIPTION: SEQ ID NO:94:

ACCTGACTCC TGTGGAGAAG TCTGCTTTTG CAGACUUCUC CACAGGAGUC AGGUGCGCGT    60

TTTCGCGC                                                                                    68

(2) INFORMATION FOR SEQ ID NO:95:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: SC3
        (B) LOCATION: 1...68
        (D) OTHER INFORMATION:

(xi) SEQUENCE DESCRIPTION: SEQ ID NO:95:

ATCTGACTCC TGAGGAGAAG ACTGCTTTTG CAGUCUUCUC CTCAGGAGUC AGAUGCGCGT    60

TTTCGCGC 68

( 2 ) INFORMATION FOR SEQ ID NO:96:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: SC4
        ( B ) LOCATION: 1...68
        ( D ) OTHER INFORMATION:

( x i ) SEQUENCE DESCRIPTION: SEQ ID NO:96:

ACCTGACTCC TGAGGAGAAG ACTGCTTTTG CAGUCUUCUC CTCAGGAGUC AGGUGCGCGT 60

TTTCGCGC 68

( 2 ) INFORMATION FOR SEQ ID NO:97:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: SC5
        ( B ) LOCATION: 1...68
        ( D ) OTHER INFORMATION:

( x i ) SEQUENCE DESCRIPTION: SEQ ID NO:97:

GCGCGTTTTC GCGCACCUGA CUCCTGTGGA GAAGUCUGCT TTTGCAGACT TCTCCACAGG 60

AGTCAGGT 68

( 2 ) INFORMATION FOR SEQ ID NO:98:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Delta
        ( B ) LOCATION: 1...25
        ( D ) OTHER INFORMATION:

( x i ) SEQUENCE DESCRIPTION: SEQ ID NO:98:

ATCTGACTCC TGAGGAGAAG ACTGC 25

( 2 ) INFORMATION FOR SEQ ID NO:99:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:99:

| CACCTGACTC CTGAGGAGAA GTCTGCC | 27 |
|---|---|

( 2 ) INFORMATION FOR SEQ ID NO:100:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:100:

| GAAGTTGGTG GTGAGGCCCT GGGCAGG | 27 |